(12) United States Patent
Ikemura et al.

(10) Patent No.: US 7,803,850 B2
(45) Date of Patent: Sep. 28, 2010

(54) CAMPHORQUINONE DERIVATIVE HAVING ACYLPHOSPHINE OXIDE GROUP, PHOTOPOLYMERIZATION INITIATOR AND PHOTO/CHEMICAL POLYMERIZATION INITIATOR CONTAINING THE SAME AND HARDENABLE COMPOSITION CONTAINING THE SAME

(75) Inventors: Kunio Ikemura, Kyoto (JP); Kensuke Ichizawa, Kyoto (JP); Yoshiyuki Jogetsu, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 253 days.

(21) Appl. No.: 12/225,070

(22) PCT Filed: Mar. 13, 2006

(86) PCT No.: PCT/JP2006/304911
§ 371 (c)(1),
(2), (4) Date: Sep. 12, 2008

(87) PCT Pub. No.: WO2007/105296
PCT Pub. Date: Sep. 20, 2007

(65) Prior Publication Data
US 2009/0105361 A1    Apr. 23, 2009

(51) Int. Cl.
*C08F 2/50*  (2006.01)
*C07F 9/02*  (2006.01)

(52) U.S. Cl. .............. 522/47; 522/48; 522/57; 522/64; 522/65; 528/15

(58) Field of Classification Search ............ 522/47, 522/48, 57, 64, 65; 568/15
See application file for complete search history.

(56) References Cited

U.S. PATENT DOCUMENTS 5,410,060 A    4/1995   Schroeder et al.
5,607,985 A *  3/1997   Masuhara et al. ............. 522/28

FOREIGN PATENT DOCUMENTS

JP      3-243602    10/1991
JP      6-247992     9/1994

OTHER PUBLICATIONS

International Search Report issued May 30, 2006 in the International (PCT) Application PCT/JP2006/304911 of which the present application is the U.S. National Stage.

* cited by examiner

*Primary Examiner*—Mark Eashoo
*Assistant Examiner*—Jessica Paul
(74) *Attorney, Agent, or Firm*—Wenderoth, Lind & Ponack, L.L.P.

(57) ABSTRACT

A compound that exhibits excellent color tone stability and physical properties as well as excellent photopolymerization activity over a wide region from near-ultraviolet to visible region, permitting relaxed operation under ambient light, so that wide application can be found in the dental field and photopolymerization industry; and a relevant photopolymerization initiator and hardenable composition. In particular, there is provided a novel camphorquinone derivative having an acylphosphine oxide group [—(C=O)—(P=O)<] in each molecule. Further, there is provided a photopolymerization initiator comprising the camphorquinone derivative having an acrylphosphine oxide group [—(C=O)—(P=O)<] in each molecule as an indispensable component, loaded with at least one member selected from among a polymerization accelerator, a photoacid generator, a photosensitizer and a (bis)acylphosphine oxide, and provided a hardenable composition comprising the initiator. The thus provided photopolymerization initiator and hardenable composition exhibit excellent color tone stability and physical properties as well as excellent photopolymeritzaion activity over an ultraviolet and visible wide wavelength region, permitting relaxed operation under ambient light, so that wide application can be found in the dental field and photopolymerization industry.

22 Claims, 2 Drawing Sheets

CAMPHORQUINONE DERIVATIVE HAVING ACYLPHOSPHINE OXIDE GROUP, PHOTOPOLYMERIZATION INITIATOR AND PHOTO/CHEMICAL POLYMERIZATION INITIATOR CONTAINING THE SAME AND HARDENABLE COMPOSITION CONTAINING THE SAME

TECHNICAL FIELD

The present invention relates to a camphorquinone derivative having an acylphosphine oxide group [—(C=O)—(P=O)<] in each molecule and a photopolymerization initiator comprising the derivative as an indispensable component. More particularly, the present invention relates to a camphorquinone derivative having an acylphosphine oxide group that exhibits photopolymerization initiation ability over a wide wavelength region from ultraviolet to visible region, permits relaxed operation under a high photo-hardening speed and ambient light and exhibits excellent color tone property of a photo-hardened product, a photopolymerization initiator comprising the derivative as an indispensable component, and a hardenable composition comprising the photopolymerization initiator.

BACKGROUND ART

A visible light polymerizing resin becomes widely used in the dental clinical field. As a photopolymerization initiator, since U. K. Patent No. 1,408,265 (Patent Document 1), a camphorquinone having a maximum absorption wavelength of 468 nm is mainly used. A hydrogen abstraction type polymerization initiation mechanism is known in which camphorquinone absorbs light to form a photoexcitation complex (exciplex) with an amine compound which is a hydrogen donor, generating an amine-derived free radical.

However, since camphorquinone has an extremely great b value expressing a tinge of yellow in the CIE Lab color specification system because of its absorption wavelength and absorbance, it is problematic to use for esthetic restorative in the dental field.

Furthermore, since an absorption wavelength of a polymerization initiation system with a combination of camphorquinone and aromatic tertiary amine is within a visible region, hardening is initiated by ambient light such as a fluorescent lamp and a dental lamp in a dental clinic room, exhibiting a high hardening speed and a short usable time. Therefore, there is a problem that a viscosity of a liquid of a bonding agent or a composite resin paste is increased upon treatment or therapy, making therapeutic operation difficult.

Patent-publication No. 2740829 (Patent Document 2) reports that 2,3-dioxobicyclo[2.2.1]heptane derivative (camphorquinone derivative) having a maximum absorption wavelength in 400 to 650 nm is a photopolymerization initiator that exhibits excellent photopolymerization ability upon polymerization of a compound having an ethylenic double bond.

Acylphosphine oxides disclosed in U.S. Pat. No. 4,265,723 (Patent Document 3) and U.S. Pat. No. 4,298,738 (Patent Document 4) is an α-cleaving type photoinitiator and generates a [—(O=)C.] radical and a [. P(=O)<] radical by C—P cleavage of an acylphosphine oxide group [—(C=O)—(P=O)<] in a molecule due to photo-irradiation. As acylphosphine oxide, so-called "bisacylphosphine oxides" that is a compound having two acyl groups in a molecule has also been put into practice, and it is disclosed in U.S. Pat. No. 4,792,632 (Patent Document 5), U.S. Pat. No. 5,721,292 (Patent Document 6) and U.S. Pat. No. 5,965,776 (Patent Document 7).

These acylphosphine oxides and bisacylphosphine oxides are widely used in the photopolymerization industry because of their great photopolymerization activity in a ultraviolet or near-ultraviolet region. Recently, they are used also in the dental field.

However, acylphosphine oxides exhibit excellent photohardening property with a halogen lamp (Hal) irradiator, but there is a disadvantage that they never become hardened have with a dental irradiator in a visible region of 430 to 500 nm, especially with a light-emitting diode (LED) irradiator and a xenon lamp (Xe) irradiator.

Japanese Patent No. 3442776 (Patent Document 8) proposes a visible light photopolymerizable adhesive consisting of a camphorquinone derivative, an acylphosphine oxide compound, at least one kind aliphatic amine and a radical polymerizable monomer.

However, a photoinitiator obtained by physically mixing them does not solve the problem of a high b value which indicates a tinge of yellow by color tone from camphorquinone at all. And also, a hardenable composition replacing aliphatic amine with aromatic amine in the photoinitiator has a problem, for use in the dental clinical field, that a color tone of a hardened product exhibits bister and a usable time is remarkably short.

That is, a photopolymerization initiator which exhibits photopolymerization activity over a wide region from nearultraviolet to visible region, manifests excellent photopolymerizability with a dental irradiator such as halogen, LED, and xenon, is excellent in color tone property of a hardened product, enhances physical properties, and can overcome an antinomy issue that "relaxed operation under high photohardening speed and ambient light", and which can be widely used in the dental field and the photopolymerization industry is desired.

Patent Document 1: U. K. Patent No. 1,408,265
Patent Document 2: Patent Publication No. 2740829
Patent Document 3: U.S. Pat. No. 4,265,723
Patent Document 4: U.S. Pat. No. 4,298,738
Patent Document 5: U.S. Pat. No. 4,792,632
Patent Document 6: U.S. Pat. No. 5,721,292
Patent Document 7: U.S. Pat. No. 5,965,776
Patent Document 8: Patent Publication No. 3442776

DISCLOSURE OF THE INVENTION

Problems to be Solved by the Invention

An object of the present invention is to solve the aforementioned problems of the previous conventional technology, and particularly, to provide a photopolymerization initiator and a photo-hardenable composition which enable photo-hardening over a wide wavelength region from ultraviolet to visible region, exhibit excellent photo-hardening property with a halogen lamp, xenon lamp, or light-emitting diode (LED) irradiator for dental clinic, improve color tone property of a photo-hardened product, enhance physical properties, and can overcome an antinomy issue that "relaxed operation under high photo-hardening speed and ambient light".

Means to Solve the Problems

The present inventors intensively studied in order to solve the aforementioned problems of the previous conventional technology and to achieve the object of the invention.

At first, as a photopolymerization initiator hardenable over a wide region from ultraviolet to visible region, the previous ternary photopolymerization initiator of camphorquinone (CQ)/acylphosphine oxide (APO)/aromatic tertiary amine was studied, and the characteristic that the initiator is hardenable over a wide wavelength region of ultraviolet and visible regions and has a high photo-hardening speed could be confirmed.

However, it was found out that the ternary photopolymerization initiator has a very short usable time under ambient light, does not improve an extremely high b value which indicates a tinge of yellow derived from camphorquinone at all and, rather, tends to be bister, thus, it has a critical problem, in terms of operability and a color tone, for use in a dental esthetic restorative material attaching importance to esthetic property and operability.

Next, the present inventors molecularly designed a novel camphorquinone derivative having an acylphosphine oxide group in each molecule. Such the camphorquinone derivative having an acylphosphine oxide group in one molecule had not existed in the past.

Performance as a photopolymerization initiator was precisely studied, and it was confirmed that a novel compound of the present invention having a camphorquinone (CQ) group and an acylphosphine oxide (APO) group in one molecule has photopolymerization initiation ability over a wide region from ultraviolet to visible region, a high photopolymerization speed, and a long visible time under ambient light. Furthermore, surprisingly, an extremely high b value indicating a tinge of yellow derived from camphorquinone is improved, and the novel compound was found out to have the characteristic being excellent in color tone property.

Thus, the present inventors found out that use of a camphorquinone derivative having an acylphosphine oxide group in each molecule as a polymerization initiator makes it possible to solve all of the previous problems and to have more excellent properties than those of a physical mixture system such as the above ternary photopolymerization initiator.

That is, the present invention provides a novel camphorquinone derivative having an acylphosphine oxide group [—(C=O)—(P=O)<] in each molecule. In the present invention, the camphorquinone derivative having an acylphosphine oxide group in each molecule includes a compound represented by the following general formula (I):

[Chemical formula 1]

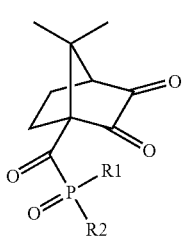

(I)

[wherein, $R^1$ is an alkyl group, an alkoxy group, or an aromatic group, each group optionally having a substituent; $R^2$ is the same as or different from $R^1$, and is an alkyl group, an alkoxy group, or an aromatic group, each group optionally having a substituent, or an —OM group, wherein M is an alkali metal or an alkaline earth metal and which may be a D body or a L body; a compound represented by the following general formula (II):

[Chemical formula 2]

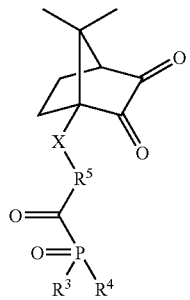

(II)

[wherein, $R^3$ is an alkyl group, an alkoxy group or an aromatic group, each group optionally having a substituent; $R^4$ is the same as or different from $R^3$, and is an alkyl group, an alkoxy group or an aromatic group, each group optionally having a substituent, or an —OM group, wherein M is an alkali metal or an alkaline earth metal; $R^5$ is a carbon atom having an aromatic group optionally having a substituent and a C2 to C18 linear chain or a substituent, as a functional group; and X is an amide bond or an ester bond] and which may be a D body or a L body; and a salt compound represented by the following general formula (III):

[Chemical formula 3]

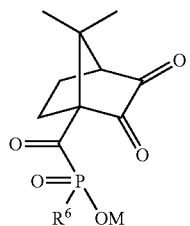

(III)

[wherein, $R^6$ is an alkyl group, an alkoxy group or an aromatic group, each group optionally having a substituent; and M is an alkali metal such as Na, K etc. or an alkaline earth metal such as Mg, Ca etc].

In the present invention, an acylphosphine oxide (APO) refers to a compound represented by the general formula:

[Chemical formula 4]

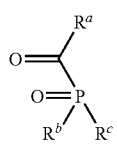

(IV)

[wherein, $R^a$, $R^b$ and $R^c$ are an arbitrary substituent], and [—(C=O)—(P=O)<] in a molecule is referred to as acylphosphine oxide (APO) group.

In this meaning, the compound represented by the general formula (IV) can be abbreviated as $R^a$-APO. For example, the compound represented by the general formula (I) is abbreviated as CQ-APO in some cases.

The present invention provides a photopolymerization initiator comprising the camphorquinone derivative having an acylphosphine oxide group [—(C=O)—(P=O)<] in each molecule as an indispensable component.

The present invention also provides a photopolymerization initiator containing one or more selected from a polymerization accelerator, a photoacid generator, a photosensitizer and (bis)acylphosphine oxide, in addition to the above camphorquinone derivative. Herein, the polymerization accelerator is selected from the group consisting of an amine compound, a barbituric acid derivative and an organotin compound, the photoacid generator is selected from the group consisting of trihalomethyl group-substituted-1,3,5-triazine compounds, the photosensitizer is an α-diketone compound, and the (bis)acylphosphine oxide is selected from the group consisting of an acylphosphine oxide compound and a bisacylphosphine oxide compound.

The present invention also provides a photo/chemical polymerization initiator capable of initiating chemical polymerization and photopolymerization, which comprises a room temperature polymerization (chemical polymerization) initiator, in addition to the above photopolymerization initiator.

The present invention provides a hardenable composition containing the above photopolymerization initiator or photo/chemical polymerization initiator and a radical polymerizable initiator. The hardenable composition can also contain a filler.

Since the hardenable composition of the present invention contains a camphorquinone derivative having an acylphosphine oxide group in each molecule, it manifests high polymerization activity over a wide wavelength region of ultraviolet and visible regions, exhibits excellent photo-hardenability with a halogen lamp, xenon lamp, light-emitting diode (LED) irradiator for dental clinic, has a high photo-hardening speed, can permit relaxed operation under ambient light and can exert excellent color tone stability and excellent physical properties of the hardenable composition.

Effect of the Invention

Since the "camphorquinone derivative having an acylphosphine oxide group [—(C=O)—(P=O)<] in each molecule" newly-created by the present invention and a photopolymerization initiator comprising the derivative as an indispensable component manifest high polymerization activity over a wide wavelength region of ultraviolet and visible regions, the hardenable composition comprising the photopolymerization initiator of the present invention exhibits excellent photo-hardenability with a halogen lamp, a xenon lamp, or a light-emitting diode (LED) irradiator for dental clinic, has a high photo-hardening speed, permits relaxed operation under ambient light and can exert excellent color tone stability and physical properties of a hardened product.

For this reason, the derivative of the present invention, a photopolymerization initiator containing the same as an indispensable component and a hardenable composition comprising the photopolymerization initiator can be applied to photo-hardenable compositions not only in the dental field and the orthopedic surgery field but also in the photopolymerization industry.

BEST MODE FOR CARRYING OUT THE INVENTION

Figure 1:
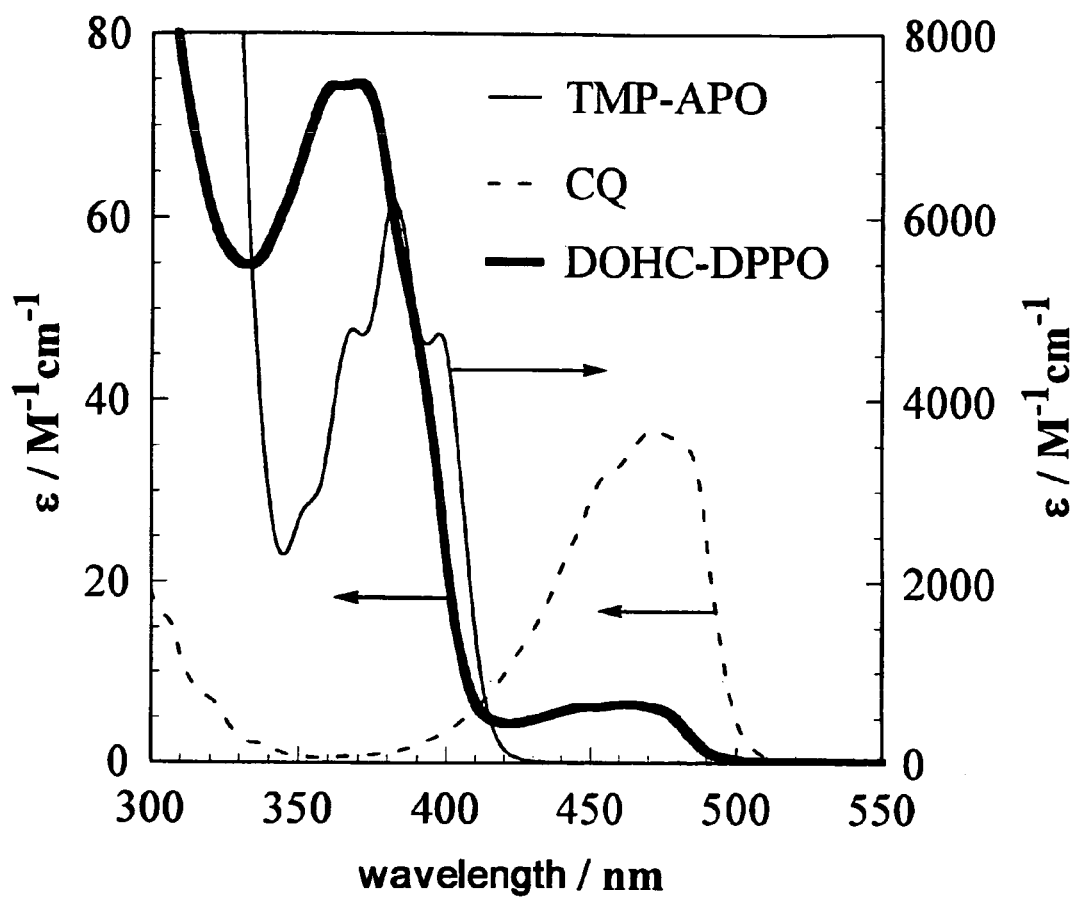
FIG. 1 An ultraviolet-visible absorption spectrum (before light irradiation) of DOHC-DPPO, CQ and TMP-APO.

The present invention relates to a photopolymerization initiator comprising a novel camphorquinone derivative having an acylphosphine oxide group in each molecule, and (A) a camphorquinone derivative having an acylphosphine oxide group in each molecule as an indispensable component and, further, comprising (B) one or more selected from a polymerization accelerator, a photoacid generator, a photosensitizer and (bis)acylphosphine oxide, and it maximally manifests its effect in a photo-hardenable composition comprising the derivative, the photopolymerization initiator and a radical polymerizable monomer.

The "camphorquinone derivative having an acylphosphine oxide group in each molecule" of the present invention includes, for example, a compound in which camphorquinone having its maximum absorption wavelength in a visible region and acylphosphine oxide having its maximum absorption wavelength in a near-ultraviolet are bound, and it can be molecularly-designed innumerably as follows.

The camphorquinone derivative having an acylphosphine oxide group in each molecule, which is the compound of the present invention, is a "substance characterized by having an α-diketone group and an acylphosphine oxide group in each molecule" in a broad sense, the substance being a compound having a hydrogen abstraction group and an α-cleavable group in one molecule.

This is, that is, such a compound that when the compound of the present invention coexists with a hydrogen donor, they are photoexcited to form an exciplex between a hydrogen donor and an α-diketone group, thereby, generating a free radical derived from a hydrogen donor, or even when the compound does not coexist with a hydrogen donor, it can permit generation of a [—(O=)C.] radical and a [.P(=O)<] radical by α-cleavage (C—P cleavage) of a [—(C=O)—(P=O)<] bond in a molecule. That is, the compound of the present invention creates the function which can be defined as "compound allowing for a hydrogen abstraction type polymerization initiation mechanism and an α-cleavage photopolymerization initiation mechanism".

A first aspect of the "camphorquinone derivative having an acylphosphine oxide group in each molecule" of the present invention includes a compound (CQ-APO), in which a camphorquinone (CQ) group and an acylphosphine oxide (APO) group are directly bound.

Such the compound includes a compound represented by the general formula (I):

[Chemical formula 5]

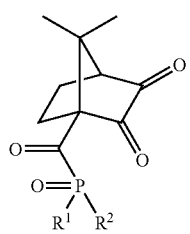

(I)

[wherein $R^1$ is an alkyl group, an alkoxy group, or an aromatic group, each group optionally having a substituent; $R^2$ is the same as or different from $R^1$, and is an alkyl group, an alkoxy group, or an aromatic group, each group optionally having a substituent, or an —OM group, wherein M represents an alkali metal or an alkaline earth metal] and which may be a D body or a L body.

Such the compound represented by the general formula (I) can be synthesized by the following synthesis route.

[Chemical formula 6]

By changing a kind of a camphorquinone derivative optionally having a substituent at 1, 4 to 7 positions other than 2,3-positional diketone and a kind of phosphite as a raw material, a number of CQ-APO derivatives represented by the general formula (I) in which $R^1$ and $R^2$ are changed, can be synthesized.

As an embodiment of a CQ-APO derivative, synthesis of 7,7-dimethyl-2,3-dioxobicyclo[2.2.1]heptane-1-carbonyl-diphenylphosphine oxide (DOHC-DPPO) is exemplified.

First, D,L-10-camphorsulfonyl chloride and potassium permanganate are reacted to synthesize D,L-ketopinic acid. D,L-ketopinic acid and selenium dioxide are reacted to synthesize, as α-diketone (DOHCA), 7,7-dimethyl-2,3-dioxobicyclo[2.2.1]heptane-1-carboxylic acid having a structure in which a carboxyl group is introduced into D,L-camphorquinone. Furthermore, DOHCA and thionyl chloride are reacted to synthesize 7,7-dimethyl-2,3-dioxobicyclo[2.2.1]heptane-1-carboxylic acid chloride (DOHCC).

[Chemical formula 7]

By the Michaelis-Arbuzov rearrangement reaction of the synthesized acid chloride (DOHCC) and methoxydiphenylphosphine[CH$_3$O—P—(Ph)$_2$], an objective substance of 7,7-dimethyl-2,3-dioxobicyclo[2.2.1]heptane-1-carbonyl-diphenylphosphine oxide (DOHC-DPPO) can be synthesized. By this rearrangement reaction, trivalent phosphorus is converted into pentavalent phosphorus to produce a phosphine oxide group [>P(=O)—].

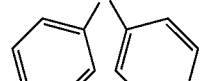

[Chemical formula 8]

DOHCC

DOHC-DPPO

As a second aspect of the "camphorquinone derivative having an acylphosphine oxide group in each molecule" of the present invention, there is exemplified a compound (CQ-L-APO) in which a camphorquinone (CQ) group and an acylphosphine oxide (APO) group are bound via a bridging group (L). Examples of the crosslinking group L include an amide bond, an ester bond, and a bridging group in which an amide bond or an ester bond and an aliphatic group or an aromatic group optionally having a substituent are bound.

Examples of such the compound include a compound represented by the following general formula (II):

[Chemical formula 9]

(II)

[wherein, $R^3$ is an alkyl group, an alkoxy group, or an aromatic group, each group optionally having a substituent; $R^4$ is the same as or different from $R^3$, and is an alkyl group, alkoxy group, or an aromatic group, each group optionally having a substituent, or an —OM group, wherein M is an alkali metal or an alkaline earth metal; $R^5$ is a carbon atom having an aromatic group optionally a substituent, and a C2 to C18 linear chain or a substituent, as a functional group; and X is an amide bond or an ester bond], and which may be a D body or a L body.

Such the compound represented by the general formula (II) can be synthesized by the following synthesis route. Herein, in the case of the compound in which X is an amide bond, a route for reacting 7,7-dimethyl-2,3-dioxobicyclo[2.2.1]heptane-1-carboxylic acid chloride (DOHCC) and an amino group-containing carboxylic acid, and synthesizing acid chloride from the produced carboxylic acid will be explained.

[Chemical formula 10]

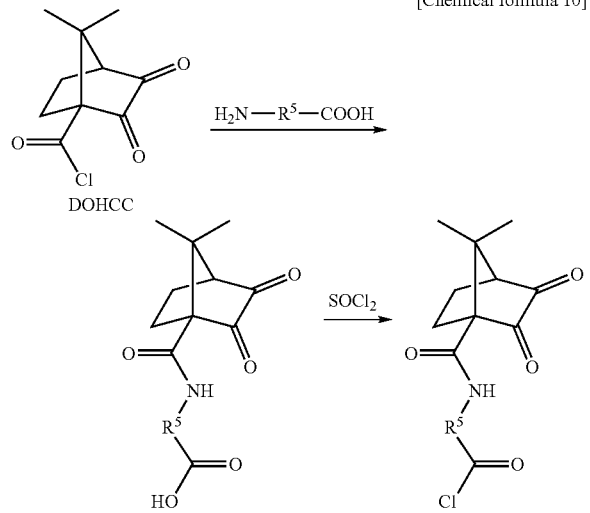

By the Michaelis-Arbuzov rearrangement reaction of the acid chloride and a methoxyphosphine compound, the compound represented by the general formula (II) of the present invention can be synthesized.

[Chemical formula 11]

In this synthesis method, the compound of the present invention can be synthesized by changing $R^5$ of the general formula (II) by arbitrarily changing a camphorquinone derivative optionally having a substituent at 1, 4 to 7 positions other than 2,3-positional diketone of a norbornene skeleton, and a starting material into infinite amino group-containing carboxylic acids such as aminobenzoic acid and aminobenzoic acid derivative such as aminosalicylic acid, and α-amino acids and amino alkylcarboxylic acid, and/or changing $R^3$ and $R^4$ of the general formula (II) by changing a kind of phosphite as a raw material for the Michaelis-Arbuzov rearrangement reaction.

A synthesis example of such the compound is exemplified. First, 7,7-dimethyl-2,3-dioxobicyclo[2.2.1]heptane-1-carboxylic acid chloride (DOHCC) and 4-aminobenzoic acid are reacted to bind D,L-camphorquinone and 4-aminobenzoic acid by an amide bond, and newly produced carboxylic acid is converted into acid chloride to synthesize p-(7,7-dimethyl-2,3-dioxobicyclo[2.2.1]heptane-1-carbonyl)-aminobenzoic acid chloride (DOHC-ABC).

[Chemical formula 12]

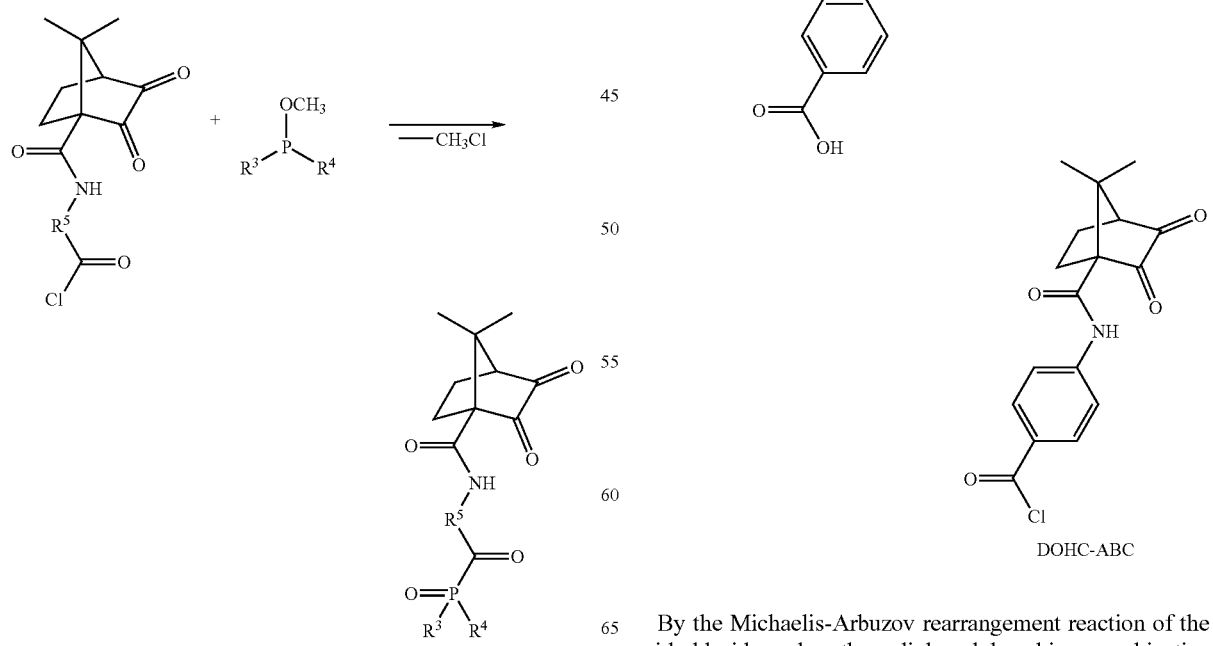

By the Michaelis-Arbuzov rearrangement reaction of the acid chloride and methoxydiphenylphosphine, an objective substance of p-(7,7-dimethyl-2,3-dioxobicyclo[2.2.1]heptane-1-carbonyl)-aminobenzoyl diphenylphosphine oxide (DOHC-AB-DPPO) can be synthesized.

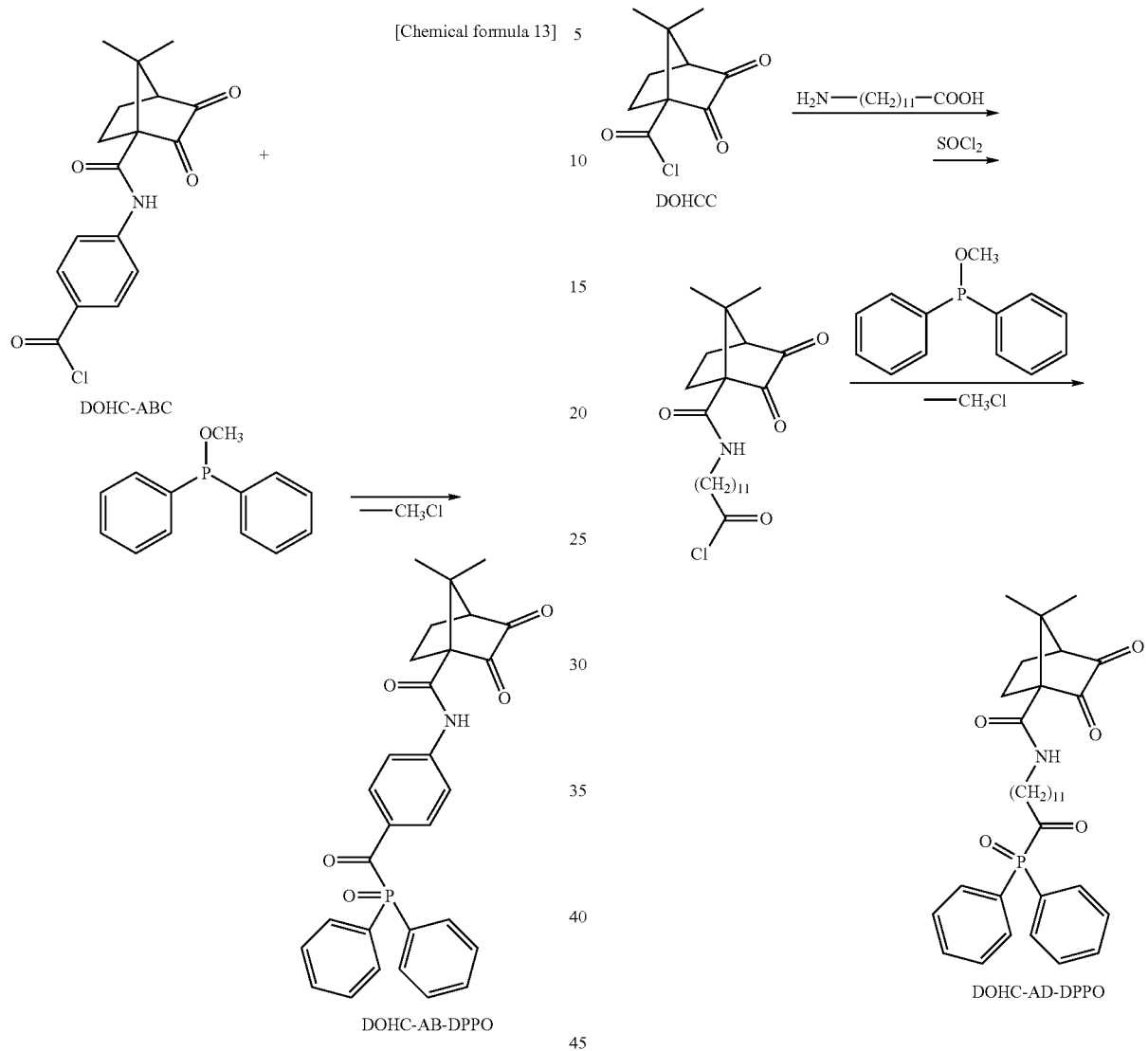

In the method of synthesizing the compound represented by the general formula (II), a number of compounds of the present invention can be synthesized by arbitrarily replacing 4-aminobenzoic acid as a starting material with amino group-containing carboxylic acids such as 4-amino-n-butyric acid, 4-amino-iso-butyric acid, 4-amino-n-caprylic acid, tranexamic acid, aminosalicylic acid, 12-aminododecanoic acid, 4-nitroanthranilic acid, 4-aminophenylacetic acid, L-glycine, L-alanine, L-valine, L-leucine, L-isoleucine, L-serine, L-homoserine, L-threonine, L-phenylalanine, L-tyrosine, L-cystine, L-benzyl-L-cystine, methionine, D,L-aspartic acid, L-glutamic acid, L-tryptophan, L-proline, L-hydroxyproline, pyrrole-2-carboxylic acid, 2-pyrrolidone-5-carboxylic acid, and phenylglycine.

By using 12-aminododecanoic acid in place of 4-aminobenzoic acid as a starting material in synthesis of the compound represented by the general formula (II), an objective substance of p-(7,7-dimethyl-2,3-dioxobicyclo[2.2.1]heptane-1-carbonyl)-aminododecane-diphenylphosphine oxide (DOHC-AD-DPPO) can be synthesized.

In the method of synthesizing the compound represented by the general formula (II), when a compound having two amino groups and two carboxyl groups such as 2,6-diaminopimelic acid is used as a raw material, a compound having two camphorquinone residues and two acylphosphine oxide groups in each molecule can be synthesized. When L-lysine is used as a raw-material, a compound having two camphorquinone residues and one acylphosphine oxide group in each molecule can be synthesized, which is related to the compound of the present invention.

Further, a compound in which X of the compound represented by the general formula (II) is an ester bond can be synthesized can as follows: For example, D,L-camphorquinone acid chloride (DOHCC) and hydroxy group-containing carboxylic acid are reacted, acid chloride is synthesized from produced carboxylic acid, and acid chloride and methoxydiphenylphosphine can be subjected to the Michaelis-Arbuzov rearrangement reaction to synthesize an objective substance of the present invention. In the thus synthesized compound of the present invention, camphorquinone and a group containing an acylphosphine oxide bond are bound with an ester group.

In these synthesis methods, a number of compounds of the present invention can be synthesized by arbitrarily changing a camphorquinone derivative optionally having a substituent at 1, 4 to 7 positions other than 2,3-positional diketone of a norbornene skeleton and a starting material into hydroxy group-containing carboxylic acid, and/or changing a kind of phosphites to change $R^3$, $R^4$, and $R^5$ of the compound represented by the general formula (II).

By replacing methoxydiphenylphosphine with dimethoxyphenyl phosphite in synthesis of the compounds represented by the general formula (I) and (II) of the present invention, methoxyphenylphosphine oxide of the compound represented by the general formula (I) and formula (II) can be synthesized.

A an example of synthesizing a water-soluble compound in which $R^2$ or $R^4$ of the compound represented by the general formula (I) or (II) as the compound of the present invention is replaced with a salt of an alkali metal or an alkaline earth metal ion, the water-soluble compound can be synthesized by applying the method disclosed in EP No. 0009348 or JP-A No. 57-197286.

When $R^2$ or $R^4$ is a substituent in a form of a salt in which a metal is ionically bound (e.g. —OM group), there is exemplified a salt compound represented by the general formula (III):

[Chemical formula 15]

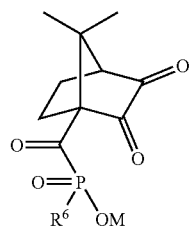

(III)

[wherein $R^6$ is an alkyl group, an alkoxy group or an aromatic group, each group optionally having a substituent; and M is an alkali metal such as Na, K, etc., or an alkaline earth metal such as Mg, Ca etc.]

As an example of synthesis of the compound represented by the general formula (III), for example, 7,7-dimethyl-2,3-dioxobicyclo[2.2.1]heptane-1-carbonyl-methoxyphenylphosphine oxide (DOHC-MPPO) corresponding to the compound represented by the general formula (I) is synthesized by the Michaelis-Arbuzov rearrangement reaction between 7,7-dimethyl-2,3-dioxobicyclo[2.2.1]heptane-1-carboxylic acid chloride (DOHCC) and dimethoxyphenylphosphine [$(CH_3O)_2$—P-Ph]. Further, the DOHC-MPPO can be reacted with sodium iodide to synthesize 7,7-dimethyl-2,3-dioxobicyclo[2.2.1]heptane-1-carbonyl-phenylphosphine oxide sodium salt (DOHC-PPO—Na).

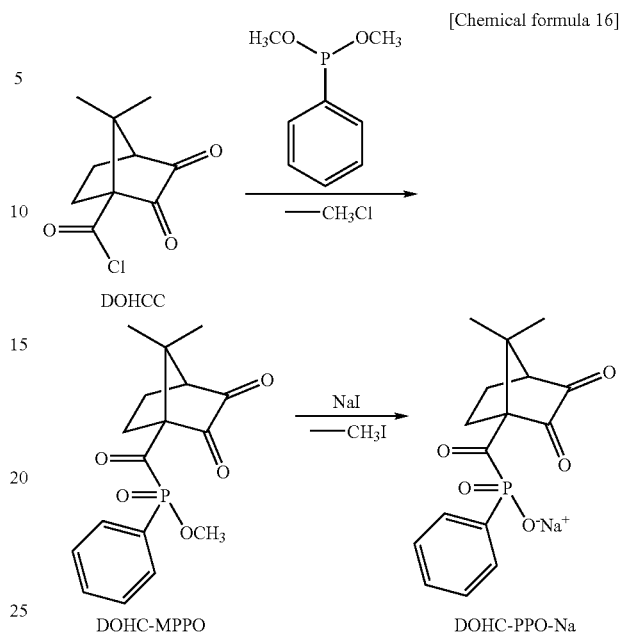

Daring to avoid infinite exemplification, it is needless to say that the present invention includes not only general formulas (I) to (III), but also all compounds consisting with definition of the "camphorquinone derivative having an acylphosphine oxide in each molecule".

Further, as far as the compound of the present invention is concerned, in place of D,L-camphorquinone, a compound in which a benzyl group and an acylphosphine oxide group are bound, can be also synthesized. From 4,4'-dichlorobenzyl, and carboxylic acid which has been reacted with an amino group-containing carboxylic acid or hydroxy group-containing carboxylic acid, acid chloride is synthesized, and the Michaelis-Arbuzov rearrangement reaction can be performed as described above to synthesize a "substance having an α-diketone group and an acylphosphine oxide group in each molecule".

Further, the compound of the present invention represented by the general formulas (I) to (III) may be synthesized by applying a new process for producing acylphosphine oxide described in JP-A No. 2006-500410.

As explained above, an infinite number of camphorquinone derivatives having an acylphosphine oxide group in each molecule of the present invention can be synthesized by the method of synthesizing compounds represented by the general formulas (I) to (III).

Examples of the compound represented by the general formula (I) include 7,7-dimethyl-2,3-dioxobicyclo[2.2.1]heptane-1-carbonyl-diphenylphosphine oxide, 7,7-dimethyl-2,3-dioxobicyclo[2.2.1]heptane-1-carbonyl-methoxyphenylphosphine oxide, 7,7-dimethyl-2,3-dioxobicyclo[2.2.1]heptane-1-carbonyl-ethoxyphenyl phosphine oxide, and 7,7-dimethyl-2,3-dioxobicyclo[2.2.1]heptane-1-carbonyl-bis(o-toluoyl)phosphine oxide.

Examples of the compound represented by the general formula (II) include p-(7,7-dimethyl-2,3-dioxobicyclo[2.2.1]heptane-1-carbonyl)-aminobenzoyldiphenylphosphine oxide, p-(7,7-dimethyl-2,3-dioxobicyclo[2.2.1]heptane-1-carbonyl)-aminobenzoyl-ethoxyphenylphosphine oxide, p-(7,7-dimethyl-2,3-dioxobicyclo[2.2.1]heptane-1-carboxyl)-aminobenzoyl-bis(o-toluoyl)phosphine oxide, p-(7,7-dimethyl-2,3-dioxobicyclo[2.2.1]heptane-1-carbonyl)-amino-n-butyl-diphenylphosphine oxide, p-(7,7-dimethyl-2,3-dioxobicyclo[2.2.1]heptane-1-carbonyl)-aminododecane-diphenylphosphine oxide, p-(7,7-dimethyl-2,3-dioxobicyclo[2.2.1]heptane-1-carbonyl)-amino-n-butyl-ethoxyphenylphosphine oxide, p-(7,7-dimethyl-2,3-dioxobicyclo[2.2.1]heptane-1-carbonyl)-aminododecane-ethoxyphenylphosphine oxide, and p-(7,7-dimethyl-2,3-dioxobicyclo[2.2.1]heptane-1-carbonyl)aminododecane-bis(o-toluoyl)phosphine oxide.

Examples of the compound represented by the general formula (III) include a 7,7-dimethyl-2,3-dioxobicyclo[2.2.1]heptane-1-carbonyl-phenylphosphine oxide sodium salt, a 7,7-dimethyl-2,3-dioxobicyclo[2.2.1]heptane-1-carbonyl-phenylphosphine oxide potassium salt, a p-(7,7-dimethyl-2,3-dioxobicyclo[2.2.1]heptane-1-carbonyl)-aminobenzoyl-phenylphosphine oxide sodium salt, and a p-(7,7-dimethyl-2,3-dioxobicyclo[2.2.1]heptane-1-carbonyl)-aminobenzoyl-phenylphosphine oxide potassium salt.

As the camphorquinone derivative having an acylphosphine oxide group in each molecule of the present invention, among those exemplified above, 7,7-dimethyl-2,3-dioxobicyclo[2.2.1]heptane-1-carbonyl-diphenylphosphine oxide, 7,7-dimethyl-2,3-dioxobicyclo[2.2.1]heptane-1-carbonyl-methoxyphenylphosphine oxide, p-(7,7-dimethyl-2,3-dioxobicyclo[2.2.1]heptane-1-carbonyl)-aminobenzoyldiphenylphosphine oxide, p-(7,7-dimethyl-2,3-dioxobicyclo[2.2.1]heptane-1-carbonyl)-aminododecanediphenylphosphine oxide, and 7,7-dimethyl-2,3-dioxobicyclo[2.2.1]heptane-1-carbonyl-phenylphosphine oxide sodium salt are particularly preferable.

An incorporation amount of the camphorquinone derivative having an acylphosphine oxide group in each molecule of the present invention is 0.001% by weight to 20% by weight, preferably 0.1% by weight to 10% by weight, particularly preferably 0.2% by weight to 5% by weight based on a total amount of the radical polymerizable monomer of the present invention.

The photopolymerization initiator of the present invention comprises (A) a camphorquinone derivative having an acylphosphine oxide group in each molecule as an indispensable component, and comprises (B) one or more selected from a polymerization accelerator, a photoacid generator, a photosensitizer, and (bis)acylphosphine oxide.

As the polymerization accelerator which can be used in the present invention, compounds which have been previously used as a photopolymerization accelerator or a room temperature polymerization accelerator can be used and, particularly, amines such as aromatic amines and aliphatic amines, barbituric acids, and organotin compounds are preferable.

Examples of amines as the polymerization accelerator usable in the present invention include N,N-dimethyl-p-toluidine, N,N-diethyl-p-toluidine, N,N-di(2-hydroxyethyl)-p-toluidine, methyl 4-N,N-dimethylaminobenzoate, ethyl 4-N,N-dimethylaminobenzate, n-butoxyethyl 4-N,N-dimethylaminobenzoate, (2-methacryloyloxy)ethyl 4-N,N-dimethylaminobenzoate, dimethylamyl 4-N,N-dimethylaminobenzoate, isoamyl 4-N,N-dimethylaminobenzoate, 4-N,N-dimethylaminobenzophenone, butyl 4-N,N-dimethylaminobenzoate, N-methyldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate. Particularly, ethyl 4-N,N-dimethylaminobenzate, and isoamyl 4-N,N-dimethylaminobenzoate are preferable.

Examples of barbituric acids as the polymerization accelerator usable in the present invention include 5-butylbarbituric acid, 1,3,5-trimethylbarbituric acid, 1-cyclohexyl-5-ethylbarbituric acid, and 1-benzyl-5-phenylbarbituric acid. Barbituric acids such as 5-butylbarbituric acid, 1,3,5-trimethylbarbituric acid, 1-cyclohexyl-5-ethylbarbituric acid, and 1-benzyl-5-phenylbarbituric acid and salts thereof are particularly preferable.

Examples of the organotin compound as the polymerization accelerator usable in the present invention include di-n-buthyltin dimalate, di-n-octyltin dimalate, di-n-octyltin dilaurate, and di-n-buthyltin dilaurate. Di-n-octyltin dilaurate and di-n-buthyltin dilaurate are particularly preferable.

These polymerization accelerators may be used alone, or two or more may be combined. An incorporation amount of these polymerization accelerators is 0.001% by weight to 20% by weight, preferably 0.01% by weight to 10% by weight, particularly preferably 0.1% by weight to 3% by weight based on a total amount of the radical polymerizable monomer of the present invention. When the amount is less than 0.001% by weight, hardening becomes insufficient. And, when the amount exceeds 20% by weight, a color tone of a hardened product becomes bad.

As the photoacid generator usable in the present invention, the previously known photoacid generator can be used and, particularly, trihalomethyl group-substituted-1,3,5-triazine compound and a diphenyl iodonium salt compound are preferable.

Examples of the trihalomethyl group-substituted-1,3,5-triazine compound included in the photopolymerization initiator of the present invention include 2,4,6-tris(trichloromethyl)-1,3,5-triazine, 2,4,6-tris(tribromo)-1,3,5-triazine, 2-methyl-4,6-bis(trichloromethyl)-1,3,5-triazine, 2-methyl-4,6-bis(tribromomethyl)-1,3,5-triazine, 2-phenyl-4,6-bis(trichloromethyl)-1,3,5-triazine, 2-methyl-4,6-bis(tribromomethyl)-1,3,5-triazine, 2-(p-methoxyphenyl)-4-bis(trichloromethyl)-1,3,5-triazine, 2-(p-methoxythiophenyl)-4-bis(trichloromethyl)-1,3,5-triazine, 2-(p-chlorophenyl)-4,6-bis(trichloromethyl)-1,3,5-triazine, 2-(p-chlorophenyl)-4,6-bis(tribromomethyl)-1,3,5-triazine, 2-(2,4-dichlorophenyl)-4,6-bis(trichloromethyl)-1,3,5-triazine, 2-(p-bromophenyl)-4,6-bis(trichloromethyl)-1,3,5-triazine, 2-[2-(p-butoxyphenyl)ethenyl]-4,6-bis(trichloromethyl)-1,3,5-triazine, 2-[2-{N-hydroxyethyl-N-ethylamino}ethoxy]-4,6-bis(trichloromethyl)-1,3,5-triazine, and 2-[2-{N-hydroxyethyl-N-methylamino}ethoxy]-4,6-bis(trichloromethyl)-1,3,5-triazine. Other examples include a reaction product of a trihalomethyl group-substituted-1,3,5-triazine compound and an amine compound such as 2-[2-{N,N-bis(2-hydroxyethyl)amino}ethoxy]-4,6-bis(trichloromethyl)-1,3,5-triazine and [2-{N-hydroxyethyl-N-methylamino}ethoxy]-4,6-bis(trichloromethyl)-1,3,5-triazine.

Among these trihalomethyl group-substituted-1,3,5-triazine compounds, 2,4,6-tris(trichloromethyl)-1,3,5-triazine, and 2-(p-methoxyphenyl)-4-bis(trichloromethyl)-1,3,5-triazine are particularly preferable.

Examples of the diphenyl iodonium salt compound included in the photopolymerization initiator of the present invention include diphenyl iodonium salt compounds of chloride, bromide, tetrafluoroborate, hexafluoroborate, hexafluoroarsenate, hexafluoroantimonate, and trifluorosulfonate such as diphenyl iodonium, bis(p-chlorophenyl) iodonium, ditolyl iodonium, p-tert-butyl phenylphenyl iodonium, bis(p-tert-butylphenyl) iodonium, bis(m-nitrophenyl) iodonium, methoxyphenyl iodonium, p-octyloxyphenyl iodonium and the like. Particularly, a diphenyl iodonium salt compound of hexafluoroborate and hexafluoroantimonate is preferable.

These photoacid generators such as trihalomethyl group-substituted-1,3,5-triazine compound and a diphenyl iodonium salt compound can be applied not only as an initiator in radial polymerization but also as a cationic polymerization initiator of a photohardenable composition consisting of an epoxy compound or an oxetane compound by using with the compound of the present invention.

An incorporation amount of the photoacid generator in the present invention is 0.005 to 15 parts by weight, preferably 0.01 to 5 parts by weight, further preferably 0.1 to 3 parts by weight based on 100 parts by weight of a radical polymerizable monomer or a cationic polymerizable monomer.

Examples of the photosensitizer usable in the present invention include an α-diketone compound, for example, diacetil, benzil, 4,4'-dimethoxybenzil, 4,4'-oxybenzil, 4,41-chlorobenzil, camphorquinone, camphorquinonecarboxylic acid, 2,3-pentadione, 2,3-octadione, 9,10-phenanthrenequinone, and acenaphthenequinone. Particularly, camphorquinone is preferable.

Abbreviation of (bis)acylphosphine oxide usable in the present invention means acylphosphine oxide and bisacylphosphine oxide.

Examples of acylphosphine oxides usable in the present invention include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbezoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate.

Example of bisacylphosphine oxides usable in the present invention include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

Among these (bis)acylphosphine oxides, 2,4,6-trimethylbenzoyldiphenylphosphine oxide, 2,4,6-trimethylbenzoylmethoxyphenylphosphine oxide, and bis(2,4,6-trimethylbenzoyl)acylphosphine oxide are particularly preferable.

An incorporation amount of (bis)acylphosphine oxides is 0.001 to 10 parts by weight, further preferably 0.1 to 5 parts by weight based on 100 parts by weight of the radical polymerizable monomer.

Water-soluble acylphosphine oxides usable in the present invention have an alkali metal ion, an alkaline earth metal ion, a pyridinium ion or an ammonium ion in an acylphosphine oxide molecule, and examples include water-soluble acylphosphine oxides disclosed in EP No. 0009348 or JP-A No. 57-197286. Specifically, these are a 2,4,6-trimethylbenzoylphenylphosphine oxide sodium salt, a 2,4,6-trimethylbenzoylphenylphosphine oxide potassium salt, and a 2,4,6-trimethylbenzoylphenylphosphine oxide ammonium salt. Further examples include water-soluble acylphosphine oxides described in JP-A No. 2000-159621.

A coumarin compound, benzoin alkyl ethers, or α-aminoketones may be further added to the photopolymerization initiator of the present invention.

Examples of the coumarin compound usable in the present compound include 3,3'-carbonylbis(7-diethylaminocoumarin) and 3,3'-carbonylbis(7-dibutylaminocoumarin).

The photo/chemical polymerization (dual cure) initiator of the present invention comprises the photopolymerization initiator of the present inventions, and further comprises a room temperature polymerization (chemical polymerization) initiator, thus, can initiate both of chemical polymerization and photopolymerization.

Examples of a chemical polymerization initiator usable in the present invention include chemical polymerization initiators such as a combination of amines and organic peroxide, a combination of organic peroxide and sufinic acid or a salt thereof, as well as a combination of amines, organic peroxide and barbituric acid derivative.

Examples of organic peroxide usable in the present invention include diacyl peroxides, peroxyesters, dialkyl peroxides, peroxy ketals, ketone peroxides, and hydroperoxides. Specifically, there are exemplified benzoyl peroxide, 2,4-dichlorobenzoyl peroxide, tert-butyl peroxybenzoate, bis-tert-butyl peroxyisophthalate, tert-butyl peroxymalecic acid, dicumyl peroxide, di-tert-butyl peroxide, lauroyl peroxide, cyclohexanone peroxide, tert-butyl hydroperoxide, p-diisopropylbenzene peroxide, bis(1-hydroxycyclohexyl peroxide), dicumyl peroxide, tert-butyl peroxybenzoate, tert-butyl peroxypivalate, tert-butyl peroxy-2-ethyl hexanoate, and lauroyl peroxide.

Particularly preferable organic peroxide includes benzoyl peroxide, and tert-butyl peroxymaleic acid.

Examples of sulfinic acid or a salt thereof usable in the present invention include p-positional toluenesulfinic acid, sodium toluenesulfinate, potassium toluenesulfinate, lithium toluenesulfinate, calcium toluenesulfinate, benzenesulfinic acid, sodium benzenesulfinate, potassium benzenesulfinate, litium benzenesulfinate, potassium benzensulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-isopropylbenzenesulfinic acid, sodium 2,4,6-isopropylbenzenesulfinate, potassium 2,4,6-isopropylbenzenesulfinate, lithium 2,4,6-isopropylbenzenesulfinate, and calcium 2,4,6-isopropylbenzenesulfinate. Sodium benzenesulfinate, and sodium p-toluenesulfinate are particularly preferable.

An incorporation amount of amines and barbituric acids usable in the present invention is indicated by the aforementioned amount range, and an incorporation amount of organic peroxide and sulfinic acid or a salt thereof is 0.01% by weight to 10% by weight, preferably 0.1% by weight to 5% by weight, particularly preferably 0.3% by weight to 3% by weight based on a total amount of the radical polymerizable monomer of the hardenable composition comprising the compound of the present invention.

The hardenable composition of the present invention comprises the photopolymerization initiator or the photo/chemical polymerization initiator of the present invention and a radical polymerizable monomer. The hardenable composition may further comprise a filler. The hardenable composition of the present invention can be used as a dental hardenable composition.

Examples of the radical polymerizable monomer usable in the present invention include radical polymerizable monomers having an unsaturated group, which have been previously used in the photopolymerization industry and the dental industry.

The radical polymerizable monomer usable in the present invention is an aliphatic or aromatic monofunctional or polyfunctional radical polymerizable monomer, and can be used by selecting from monomers, oligomers, and prepolymers having a radical polymerizable unsaturated double bond, which are used in the dental field and the general industry field. Alternatively, a polymerizable monomer having a sulfur atom in a molecule, a polymerizable monomer having a fluoroalkyl group in a molecule, and a radical polymerizable monomer having fluorine ion releasing ability can be used.

Examples of the radical polymerizable monomer in the present invention include methyl(meth)acrylate, ethyl (meth) acrylate, styrene, 2-hydroxyethyl(meth)acrylate, glycerol dimethacrylate, 2,3-dihydroxypropyl(meth)acrylate, 5-hydroxypentyl(meth)acrylate, 6-hydroxyhexyl (meth)acrylate, 10-hydroxydecyl(meth)acrylate, 3-(meth)acryloyloxyhexyl-triethoxysilane, γ-(meth)acryloyloxypropylmethoxysilane, 2,2-bis{4-(meth)acryloxypropoxyphenyl}propane; bisphenol A diglycidyl (meth)acrylate; Bis-GMA, [2,2,4-triethylhexamethylenebis(2-carbamoyloxyethyl)]di(meth)acrylate; UDMA, ethylene glycol di(meth)acrylate, triethylene glycol di(meth)acrylate, dipentaerythritol di(meth)acrylate, 1,6-hexane di(meth)acrylate, 1,10-decanediol di(meth)acrylate, pentaerythritol tetra(meth)acrylate, trimethylolpropane tri (meth)acrylate, trimethylolethane tri(meth)acrylate, tetramethylolmethane tri(meth)acrylate, 1,7-diacryloyloxy-2,2,6,6-tetraacryloyloxymethyl-4-oxyheptane N,N'-(2,2,4-trimethylhexamethylene)bis[2-(aminocarboxy)propane-1,3-diol]tetramethacrylate and, as urethane tetramethacrylates, 2:1 addition reaction product of 1,3-dimethacryloyloxy-2-hydroxypropane and 2,2,4-trimethyl diisocyanate, 6-(meth) acryloyloxyhexyl 6,8-dithioctanate, 10-(meth)acryloyloxydecyl 6,8-dithioctanate, and the like.

Herein, abbreviation of (meth)acrylate means acrylate and (meth)acrylate. Abbreviations of (meth)acryloyl and (meth) acryloxy are the same.

As the radical polymerizable monomer having a fluoroalkyl group constituted of at least one fluorocarbon, a (meth) acrylate compound having one or more polymerizable groups such as a methacryloyl group, an acryloyl group, a vinyl group or a vinylbenzyl group can be used, and examples include compounds described in JP-A No. 2003-095838, and compounds described in JP-A No. 2003-105272.

Examples of the radical polymerizable monomer having fluorine ion releasing ability usable in the present invention include cyclic phosphazene compounds described in JP-A No. 2003-342112.

These radical polymerizable monomers can be used alone or by appropriately combining them, and ethylene glycol di(meth)acrylate, triethylene glycol di(meth)acrylate, 1,6-hexane di(meth)acrylate, trimethylolpropane tri(meth)acrylate, 2,2-bis{4-(meth) acryloxypropoxyphenyl}propane=bisphenol A-diglycidyl (meth)acrylate, di(meth)acryloxyethyl-2,2,4-trimethylhexamethylenediurethane are particularly preferable.

These radical polymerizable monomers can be used alone, or by combining two or more compounds. An incorporation amount of these radical polymerizable monomers is 10% by weight to 99.9% by weight, preferably 20% by weight to 80% by weight, particularly preferably 25% by weight to 78% by weight based on a total amount of the hardenable composition containing the photopolymerization initiator of the present invention. When the amount is less than 5% by weight, or more than 99.9% by weight, hardening property is reduced.

Depending on the requirement that one wants to impart adhesion ability to the dental hardenable composition of the present invention and so on, the radical polymerizable monomer having an acidic group in a molecule may be appropriately incorporated in such a range that storage stability is possible.

As the radical polymerizable monomer having the acidic group, for example, 4-(meth)acryloxyethyltrimellitic acid, 4-(meth)acryloxyethyltrimellitic anhydride, 6-(meth)acryloxyhexyl phosphonoacetate, 6-(meth)acryloxyhexyl phosphonopropionate, and 10-(meth)acryloxydecyl hydrogen phosphate are preferable.

These radical polymerizable monomers having an acidic group in a molecule may be used alone, or two or more compounds may be combined.

An incorporation amount of these radical polymerizable monomers having an acidic group in a molecule is 0.1% by weight to 30% by weight, preferably 3% by weight to 15% by weight, particularly preferably 5% by weight to 10% by weight based on a total amount of the radical polymerizable monomer of the hardenable composition having the photopolymerization initiator. When the amount is less than 0.1% by weight, or more than 30% by weight, hardening property is reduced.

In order to adjust a mechanical strength, handling property, coating property or flowability, in addition to the radical polymerizable monomer, a filler may be appropriately incorporated into the hardenable composition comprising the photopolymerization initiator of the present invention.

Examples of the filler usable in the present invention include organic or inorganic fillers which have previously been used in the photopolymerization industry and the dental field.

A preferable filler usable in the hardenable composition of the present invention is a ultrafine particle filler, a silica filler, a polymer, and a pre-reacted glass ionomer filler (=PRG filler: preformed glass ionomer filler=filler produced by subjecting fluoroaluminosilicate glass and polyalkenoic acid to an acid-base reaction in water to produce a glass ionomer reaction gel, and drying it), described in Japanese Patent No. 3497508 (2003) and U.S. patent Ser. No. 08/892,766 (2000) filed by the present applicant.

Alternatively, these fillers may be surface-treated with the known surface treating agent such as a silane coupling agent as necessary and, thereafter, may be used. Examples of such the surface treating agent include vinyltrichlorosilane, γ-methacryloyloxypropyltrimethoxysilane, γ-glycidoxypropyltrimethoxysilane, and γ-aminopropyltriethoxysilane.

Among these fillers, a ultrafine particle filler, a silica filler, and a fluorine sustained-release filler are particularly preferable.

An organic solvent such as acetone and ethyl alcohol may be appropriately added to the hardenable composition of the present invention, and water may be further added. Water can be incorporated as necessary when the compound of the present invention is applied to an adhesive. As water, purified water or ion-exchanged water is preferable.

Examples of a polymerization inhibitor contained for stabilizing a shelf life of the hardenable composition containing the photopolymerization initiator of the present invention include hydroquinone, hydroquinone monomethyl ether, and butylated hydroxytoluene. Hydroquinone monomethyl ether and butylated hydroxytoluene are preferable.

Depending on the use purpose of the hardenable composition containing the photopolymerization initiator of the present invention, a denaturing agent, a thickener, a dye, a pigment, and a polymerization adjusting agent may be appropriately incorporated.

The hardenable composition containing the photopolymerization initiator of the present invention can be used, as an implementation aspect, in a photopolymerization bonding agent, a photopolymerization composite resin, a photopolymerization composite resin for a crown and a bridge of a tooth crown, a photo/chemical polymerization resin cement, a Fischer sealant, an adhesive for orthodontics, a teeth coating agent, an opaque agent, a photopolymerization nail material, and a photopolymerization nail adhesive.

EXAMPLES

The following Examples and Comparative Examples specifically illustrate the present invention, but the present invention is not limited by these Examples at all.

Compounds and materials other than compounds of the present invention used in Example 3 and thereafter TCT: 2,4,6-Tris(trichloromethyl)-1,3,5-triazine MCT: 2-(p-Methoxyphenyl)-4,6-bis(trichloromethyl)-1,3,5-triazine DMBE: Ethyl 4-N,N-dimethylaminobenzoate DEPT: (2-Hydroxyethyl)-p-toluidine TMBA: 1,3,5-Trimethylbarbituric acid BPBA: 1-Benzyl-5-phenylbarbituric acid CQ: Camphorquinone TMP-APO: 2,4,6-Trimethylbenzoyldiphenylphosphine oxide Bis-TMP-APO: Bis(2,4,6-trimethylbenzoyl)phenylphosphine oxide BPO: Benzoyl peroxide Bis-GMA: 2,2-Bis(4-methacryloxypropoxyphenyl)propane=bisphenol A diglycidyl methacrylate UDMA: [2,2,4-Trimethylhexamethylenebis(2-carbamoyloxyethyl)]dimethacrylate=dimethacryloyloxyethyl-2,2,4-trimethylhexamethylenediurethane EGDMA: Ethylene glycol dimethacrylate TEGDMA: Triethylene glycol dimethacrylate TMPT: Trimethylolpropane trimethacrylate 4-AET: 4-Acryloxyethyltrimellitic acid 6-MHT: (6-Methacryloxy)hexyl-3-phosphonopropionate BHT: Butylated hydroxytoluene Silica filler: (average particle size: 2 μm, silane coupling-treated)

Ultrafine particle filler: Aerosil R-972 (average particle size: 0.18 μm, manufactured by NIPPON AEROSIL CO., LTD.)

Methods of assessing a material used in Examples of the present invention will be shown below.

(1) Ultraviolet-Visible Absorption Spectrum

A spectrum was measured using a quartz cell with a spectrophotometer (manufactured by HITACHI, HITACHI U-3310) at a cell length of 1.0 cm, and a sample concentration of 0.1 mmol/L or 10 mmol/L in a toluene solvent.

(2) Photohardenability Assessment

One droplet of a solution of the prepared photohardenable composition was taken on a mixing pad, and irradiated with light using various irradiators (Hal, LED, Xe), and photohardenability was confirmed. As three kinds of dental light irradiators, a halogen lamp (Hal) irradiator, Shofu Grip Light II [manufactured by SHOFU INC.] (30 seconds irradiation, illuminance: 650 mW/cm$^2$, wavelength region: 375-525 nm, $\lambda_{max}$=500 nm), Elipar Free Light 2 (manufactured by 3M ESPE) as a light emitting diode (LED) irradiator (10 seconds irradiation, illuminance: 635 mW/cm$^2$, wavelength region: 420-510 nm, $\lambda_{max}$=455 nm) and APOLLO 95E Elite (manufactured by DMD) as a xenon lamp (Xe) irradiator (3 seconds irradiation, illuminance: 1330 mW/cm$^2$, wavelength region: 435-520 nm, $\lambda_{max}$=465, 500 nm) were used. An illuminance measuring wavelength region of each irradiator was 400-515 nm.

◎: An amount of an unreacted monomer on a surface is extremely small, and extremely high photohardenability is exhibited.

○: An amount of an unreacted monomer on a surface is small, and high photohardenability is exhibited.

Δ: An amount of an unreacted monomer on a surface is recognized, and low photohardenability is exhibited.

x: No photohardenability.

(3) Light DSC Measurement

Shofu Grip Light II (Hal) [manufactured by Shofu Inc.] using a halogen lamp, connected to a differential scanning calorimeter (Thermal Analysis System TAS 2000 DSC8230D, Rigaku Inc.) with a glass fiber was used at an illuminance: 80 mW/cm$^2$, and a wavelength region: 400-800 nm. A sample (8 mg) was placed into a mini aluminum pan, and light was irradiated in DSC through a glass fiber tip. In this light DSC measurement, a time from immediately after light irradiation to maximum heat production was measured as a light polymerization time (sec). An average was obtained at triplicate measurement of a sample.

(4) Usable Time (Sec)

A photohardenable sample (30 mg) was placed 1 m under a dental halogen lamp (Luna-Vue S, manufactured by Morita Seisakusho K. K.) of an illuminance 10,000 Lx (±2,000 Lx), and a time until gelling (sec) was measured. The sample was observed until 150 seconds at longest. Determination of a relaxed operation time was defined as 30 seconds or longer for a liquid hardenable composition and a filler-containing paste-like hardenable composition.

(5) Measurement of Color Difference of Hardened Product

Prepared various photohardenable compositions were placed into a stainless ring, pressed with two glass covers from upper and lower directions, both surfaces was irradiated with light for every 3 minutes using a photopolymerization instrument (TWIN-CURE manufactured by Shofu Inc.) to make a round plate having a diameter of 15 mm and a thickness of 2 mm. The prepared round plate was measured for a color difference by L*a*b* color specification system with a color difference meter (Color Guide, BYK-Gardner). Thereupon, a color, a L value, an a value, and a b value of immediately after preparation of a round plate, and a color difference after one day at 70° C. were measured, and ΔE and Δb were determined. ΔE and Δb are calculated as follows. Further, color difference before and after photohardening ΔE and Δb were determined.

$$\Delta E = \sqrt{(L_f - L_i)^2 + (a_f - a_i)^2 + (b_f - b_i)^2}$$

$$\Delta b = b_f - b_i$$

In the above equation, $L_i$, $a_i$ and $b_j$ are respective values immediately after around plate preparation, and $L_f$, $a_f$ and $b_f$ are respective values from measurement of the prepared round plate after one day at 70° C.

(6) Hardening Depth (=Depth of Cure) (mm)

A sample was filled into an internal diameter 4 mm×height 8 mm, upper and lower sides of this was pressed with cover glasses, and irradiated with light for 30 seconds using a halogen lamp (Grip Light II manufactured by Shofu Inc.) while an upper side was contacted with a glass cable tip. After photohardening, a mold was removed, a photohardened product was taken out, a light-irradiated back side was wiped with a bleached cotton cloth impregnated with an alcohol, and a length of a remaining hardened product was determined, which was adopted as a photohardening depth (mm).

(7) Hardness

An experimentally manufactured photopolymerized composite resin was charged into a stainless mold having a diameter of 4 mm and a height of 2 mm, upper and lower sides of the mold were contacted under a pressure with a thin slide glass, and this was placed on a white mixing pad, and irradiated with light for 30 seconds as in the "hardening depth" while a one glass side was directly contacted with a cable tip of an irradiator. After photohardening, a mold was removed, a photohardened product was taken out, and a hardness test body was prepared. A Vickers hardness (Micro Hardness Tester: manufactured by Matsuzawa Seiki Co., Ltd.) of an irradiated side (surface side) and a back side of the hardened product.

Using a Vickers indenter, a Vickers hardness from a ratio of lengths of diagonal lines of an indent generated in a test piece was measured at a load of 100 gf, and a load preserving time of 30 seconds.

(8) Flexural Strength, Elastic Modulus

Based on ISO specification, a flexural strength test piece (2×2×25, mm) was made, placed in water at 37° C. for 24 hours, and a flexural strength and an elastic modulus were measured by a three-point flexural strength test at a distance between the supports of 20 mm. Light irradiation was performed with Grip Light II (Hal) (manufactured by Shofu Inc.).

Example 1

Synthesis of 7,7-dimethyl-2,3-dioxobicyclo[2.2.1]heptane-1-carbonyl-diphenylphosphine oxide (DOHC-DPPO)

Step 1: Synthesis of 7,7-dimethyl-2,3-dioxobicyclo[2.2.1]heptane-1-carboxylic acid (DOHCA)

[Chemical formula 17]

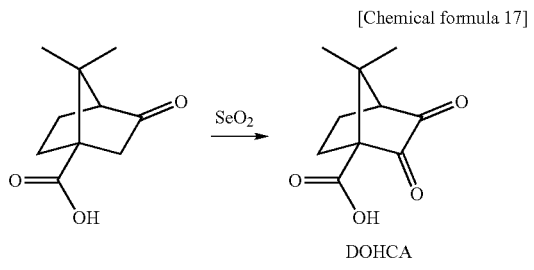

DOHCA

In 50 mL of acetic acid, 9.1 g (50 mmol) of 2-oxo-1-apocamphancarboxylic acid (D,L-ketopic acid) and 7.77 g (70 mmol) of selenium dioxide were refluxed for 18 hours and, after cooling, the reaction mixture of evaporated to dryness. The residue was dissolved in ethyl acetate, and washed with water. The ethyl acetate layer was dried with sodium sulfate, filtered and concentrated. The residue was recrystallized from ethyl acetate and hexane to obtain 8.2 g (yield 83%) of the title compound (DOHCA).

Melting point 239° C.
IR spectrum (neat: $cm^{-1}$): 1766.52, 1749.51 ($\nu C{=}O$ of $\alpha$-diketone), 1693.57 ($\nu C{=}O$ of —COOH)

Step 2: Synthesis of 7,7-dimethyl-2,3-dioxobicyclo[2.2.1]heptane-1-carboxylic acid chloride (DOHCC)

[Chemical formula 18]

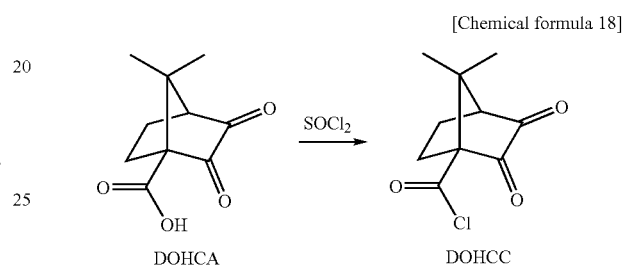

DOHCA     DOHCC

To 16 g (0.075 mmol) of 2,3-diketocarboxylic acid (DOHCA) was added 80 mL (1.10 mmol) of thionyl chloride, they were reacted for 1 hour under heat refluxing, and the excessive reaction solution was evaporated to dryness with an evaporator. Further, in order to remove a minor amount of thionyl chloride, carbon tetrachloride was added, followed by concentration again. To the resulting waxy residue was added n-hexane to crystallize to obtain 16.1 g (yield 92.2%) of the titled compound.

The product showed a pale yellow crystal which was less yellowish than CQ of a yellow crystal.

Melting point: 121 to 124° C.
IR spectrum (neat: $cm^{-1}$): 1776.44 ($\nu C{=}O$ of COCl)
Elementary analysis: for $C_{10}H_{11}ClO_3$,
cal'd: C, 55.96%; H, 5.17%
found: C, 56.18%; H, 5.33%

Step 3: Synthesis of 7,7-dimethyl-2,3-dioxobicyclo[2.2.1]heptane-1-carbonyl-diphenylphosphine oxide (DOHC-DPPO)

[Chemical formula 19]

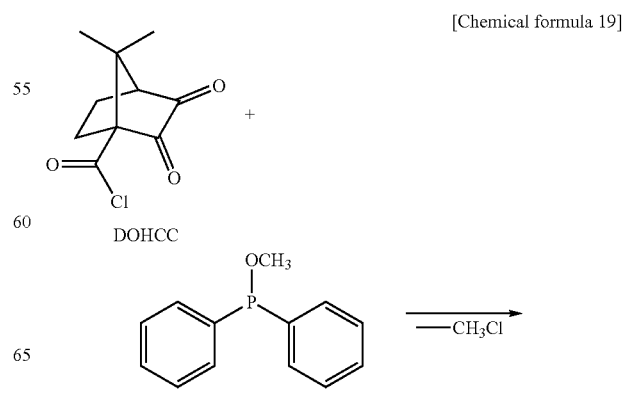

-continued

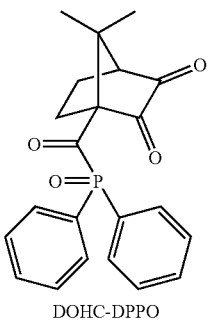

DOHC-DPPO

Acid chloride (DOHCC) (5.0 g, 23.30 mmol) synthesized in Step 2 and 5.1 g (23.75 mmol) of methoxydiphenylphosphine were reacted at 65° C. for 5 hours in a dark chamber. A reaction time was determined by a time at which 1776.44 cm$^{-1}$ (vC=O of COCl) completely disappeared on an IR spectrum. After completion of the reaction, vC=O (1697.36 cm$^{-1}$) and vP=O (1188.15 cm$^{-1}$) of an acylphosphine oxide group were produced. The reaction mixture was concentrated, and placed into a large amount of hexane (200 mL), and a precipitate was filtered and washed to obtain 7.7 g (yield 86.0%) of the title compound (DOHC-DPPO).

The product showed a pale yellow crystal which was less yellowish than CQ of a yellow crystal.

Melting point: 92.1° C.

IR spectrum (neat: cm$^{-1}$): 1749.44 (vC=O of 0 α-diketone), 1697.36 [vC=O of —C(=O)—P(=O)<], 1188.15 [vP=O of —C(=O)—P(=O)<]

Elementary analysis: for $C_{22}H_{21}O_4P$, cal'd: C, 69.47%; H, 5.56%. found: C, 69.16%: H, 5.71%

Ultraviolet-visible spectrum (solvent: toluene): Continuous wide absorption was shown at 350-500 nm, and a maximum absorption wavelength $\lambda_{max}$=370 nm (derived from acylphosphine oxide group) and $\lambda_{max}$=462 nm (derived from camphorquinone group) were recognized.

From the above analysis results, a structure of synthesized DOHC-DPPO was determined as follows:

[Chemical formula 20]

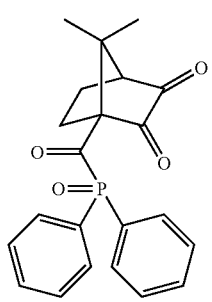

Example 1-2 (Measurement of Ultraviolet-Visible Absorption Spectrum)

Figure 2:
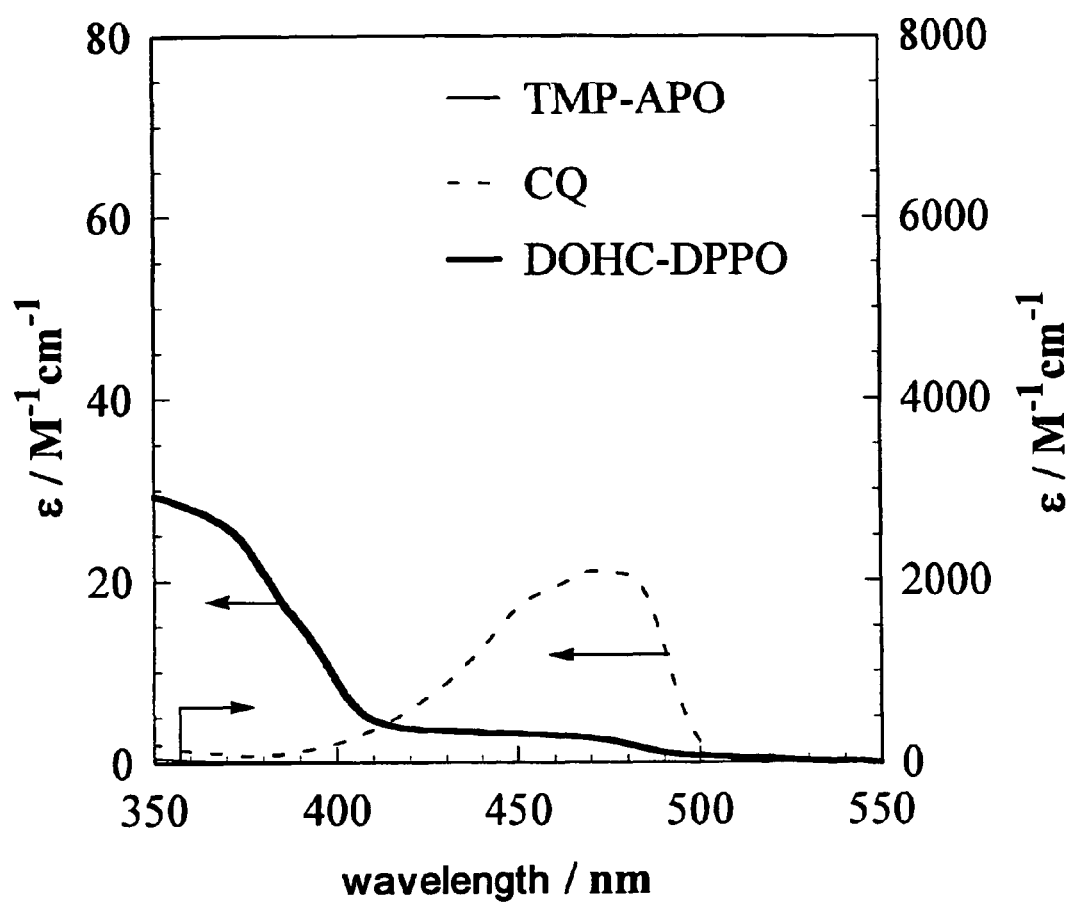
FIG. 2 An ultraviolet-visible absorption spectrum (after light irradiation) of DOHC-DPPO, CQ and TMP-APO.

An ultraviolet-visible absorption spectrum of DOHC-DPPO, CQ and TMP-APO synthesized as an embodiment of CQ-APO was measured with a spectrophotometer (HITACHI U-3310 manufactured by HITACHI co., Ltd.) in a toluene solvent using a quartz cell of a length of 1.0 cm at a concentration of 0.1 mmol/L in the case of TMP-APO, or 10 mmol/L in the case of CQ and DOHC-DPPO. Ultraviolet-visible absorption spectra before light irradiation (FIG. 1) and after irradiation (FIG. 2) with a halogen lamp are shown in FIGS. 1 and 2. A normal name and a chemical formula of CQ and TMP-APO are shown below.

CQ: D,L-camphorquinone

[Chemical formula 21]

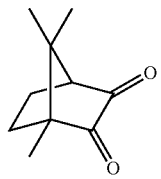

TMP-APO: 2,4,6-Trimethylbenzoyldiphenylphosphine oxide

[Chemical formula 22]

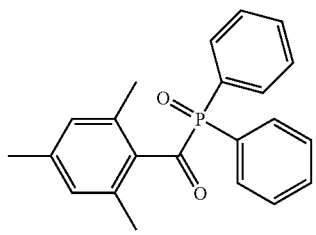

A region of a wavelength of about 400 nm to 800 nm is a visible light region, and a substance which absorbs light in this region exhibits a color. As shown in FIG. 1, CQ has absorption of an absorption coefficient $\epsilon_{max}$=37.2 M$^{-1}$ cm$^{-1}$ at $\lambda_{max}$=472 nm. Since this absorption of CQ is in a visible light region, yellow is exhibited. TMP-APO has very great absorption of an absorption coefficient $\epsilon_{max}$=6710 M$^{-1}$ cm$^{-1}$ at $\lambda_{max}$=382 nm, but since this absorption belongs to a near ultraviolet region, no color is exhibited. Consequently, TMP-APO is colorless.

On the other hand, DOHC-DPPO synthesized as an embodiment of CQ-APO has an absorption coefficient $\epsilon_{max}$=74.6 M$^{-1}$ cm$^{-1}$ and 7.0 M$^{-1}$ cm$^{-1}$ at $\lambda_{max}$=370 nm and 462 nm, respectively. Since absorption of DOHC-DPPO at $\lambda_{max}$=370 nm is in a near ultraviolet region as in the aforementioned TMP-APO, it is not involved in exhibiting a color. However, absorption in a visible light region at $\lambda_{max}$=462 nm is involved in exhibiting a color. When an absorption coefficient of DOHC-DPPO is compared with that of CQ, an absorption coefficient of DOHC-DPPO is about ⅕ an absorption coefficient of CQ. Due to this difference in an absorption coefficient, DOHC-DPPO exhibits very pale yellow as compared with yellow exhibited by CQ, thereby, it is presumed that a Δb value before and after hardening becomes a very small value. In addition, an absorption coefficient including results after light irradiation will be described later.

From FIG. 2, TMP-APO showed an absorption coefficient $\epsilon$=19.0 M$^{-1}$ cm$^{-1}$ at $\lambda$=382 nm after light irradiation, and was reduced to 1/325 of that before light irradiation. CQ showed an absorption coefficient $\epsilon_{max}$=21.0 M$^{-1}$ cm$^{-1}$ in absorption at 472 nm after light irradiation, and was reduced to 1/1.8. In TMP-APO, by light irradiation, a C—P bond of —(C=O)—(P=O)— of an acrylphosphine oxide is cleaved to generate a radical. In addition, in TMP-APO, since a compound having a different structure from that of TMP-APO is produced, absorption at $\lambda_{max}$=382 nm of an acrylphosphine oxide bond is reduced after light irradiation. However, unlike α-cleavage type TMP-APO, in the case of CQ, slow hydrogen abstraction from a solvent toluene does not lead to considerable reduction in an absorption coefficient.

It was confirmed that DOHC-DPPO which is the compound of the present invention exhibits respective absorptions at λ=370 nm and 462 nm having an absorption coefficient $\epsilon$=26.0 M$^{-1}$ cm$^{-1}$ and 2.9 M$^{-1}$ cm$^{-1}$ after light irradiation, reducing to 1/2.8 and 1/2.4 from before irradiation. Thereby, it is suggested that, in DOHC-DPPO, radical generation due to both of C—P cleavage of an acylphosphine oxide group and hydrogen abstraction of α-diketone is possible by light irradiation.

Herein, both of TMP-APO, and DOHC-DPPO which is the compound of the present invention have a [—C(=O)—P(=O)<] bond. A [—C(=O)—P(=O)<] bond has absorption at around 370 nm, and it is understandable that absorption at around 370 nm is reduced due to C—P cleavage by light irradiation in both compounds.

In FIG. 2, an absorption coefficient of TMP-APO was considerably reduced between before and after light irradiation as compared with an absorption coefficient of DOHC-DPPO of the present invention. Reference is made to this fact so that this is not misunderstood. Since TMP-APO has a benzoyl group having a resonance structure of a benzene ring and a carbonyl group in a molecule before light irradiation, it has a great absorption coefficient by overlapping of an absorption wavelength of this benzoyl group and an absorption wavelength of a [—C(=O)—P(=O)<] bond.

After light irradiation, a benzoyl group in a molecule of TMP-APO becomes free sterically, and free rotation between a benzene ring and a carbonyl group becomes possible. As a result, it is presumed that in TMP-APO, after light irradiation, absorption peculiar to a benzoyl group disappears, and absorption peculiar to a benzene ring and absorption peculiar to a carbonyl group appear, and an absorption wavelength is shifted to a shorter wavelength side. Thereby, it is thought that an absorption coefficient of TMP-APO is considerably reduced from 6170 M$^{-1}$ cm$^{-1}$ to 19.0 M$^{-1}$ cm$^{-1}$ at 382 nm by light irradiation.

Next, regarding DOHC-DPPO of the present invention, DOHC-DPPO has originally no benzoyl group in a molecule. Therefore, since it is thought that an absorption coefficient at around 370 nm of DOHC-DPPO before light irradiation is the original value only due to a [—C(=O)—P(=O)<] bond, its absorption coefficient is 74.6 M$^{-1}$ cm$^{-1}$ at 370 nm. At this wavelength, an absorption coefficient of this DOHC-DPPO is reduced to 26.0 M$^{-1}$ cm$^{-1}$ after light irradiation.

Since this value of DOHC-DPPO is an approximately the same as the aforementioned value (19.0 M$^{-1}$ cm$^{-1}$) of TMP-APO after light irradiation, it can be understood that C—P cleavage of a [—C(=O)—P(=O)<] bond is generated in both of DOHC-DPPO and TMP-APO after light irradiation.

From the foregoing, a value of an absorption coefficient at around 370 nm does not, as it is, manifest the effect as a photoinitiator due to C—P cleavage of an acylphosphine oxide group.

Example 2

Synthesis of p-(7,7-dimethyl-2,3-dioxobicyclo[2.2.1]heptane-1-carbonyl)-aminobenzoyldiphenylphosphine oxide (DOHC-AB-DPPO)

Step 1: Synthesis of p-(7,7-dimethyl-2,3-dioxobicyclo[2.2.1]heptane-1-carbonyl)-aminobenzoic acid (DOHC-AB)

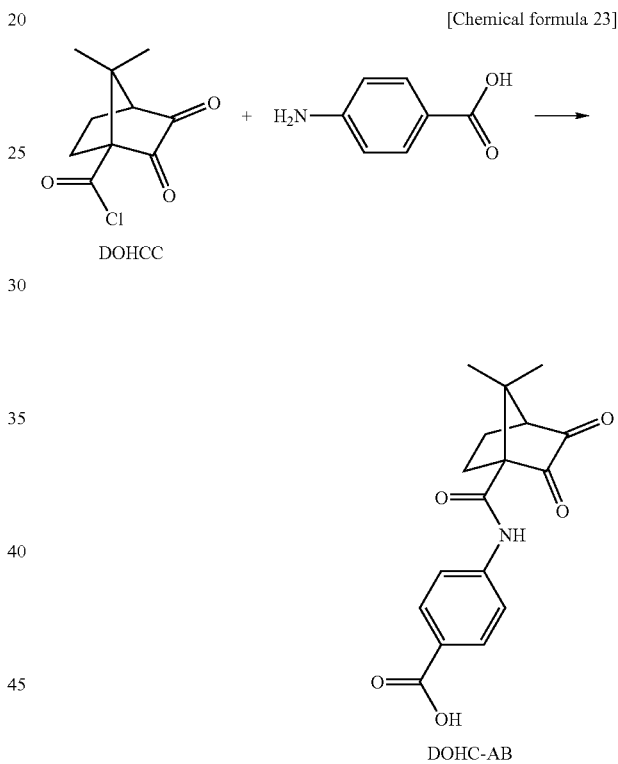

[Chemical formula 23]

P-aminobenzoic acid (4.13 g, 0.03 mol) and 8.6 g (0.06 mol) of a 28.5% aqueous sodium hydroxide solution were mixed and, when became pasty, a solution obtained by dissolving 6.45 g (0.03 mol) of 7,7-dimethyl-2,3-dioxobicyclo[2.2.1]heptane-1-carboxylic acid chloride (DOHCC) in 20 mL of toluene was added dropwise. After addition, an internal temperature was raised to 35 to 40° C., and materials were stirred to react for 2 hours. After cooling, 3.06 g (0.03 mol as 36%) of concentrated hydrochloric acid and 20 ml of water were added. After stirring continued for 30 minutes at it was, a crystal was collected by filtration, and washed with water, water was sufficiently removed, phosphorus pentaoxide was placed into a vacuum desiccator, and the crystal was dried in the vacuum desiccator to obtain the title compound.

Amount 6.6 g (yield 7%). Melting point 281-283° C.

Step 2: Synthesis of p-(7,7-dimethyl-2,3-dioxobicyclo[2.2.1]heptane-1-carbonyl)-aminobenzoic acid chloride (DOHC-ABC)

[Chemical formula 24]

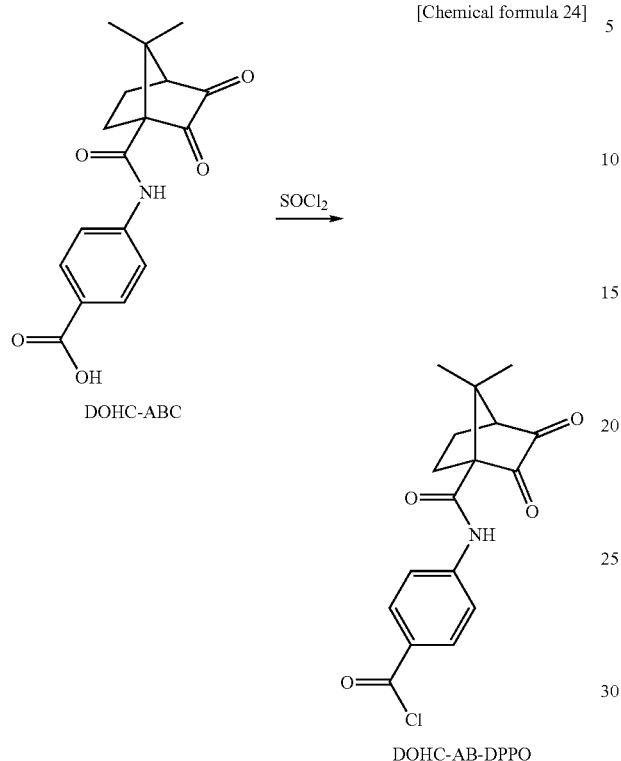

The compound (DOHC-AB) (5.5 g, 0.0174 mol) synthesized in Step 1 and 27 mL of thionyl chloride were placed, and reacted for 1 hour under refluxing. After completion of the reaction, excessive thionyl chloride was distilled off, the residue was treated with n-hexane, and a crystal was collected by filtration. This was dried with a vacuum desiccator to obtain 5.36 g of the title compound (DOHC-ABC).

Melting point 124-127° C.

IR spectrum (neat: cm$^{-1}$): 1540.02 (δ NH of —CONH—) 1680.03 (vC=O of —CONH—), 1748.55 (vC=O of COCl), 3400.02 (vNH of —CONH—)

Step 3: Synthesis of p-(7,7-dimethyl-2,3-dioxobicyclo[2.2.1]heptane-1-carbonyl)-aminobenzoyldiphenylphosphine oxide (DOHC-AB-DPPO)

[Chemical formula 25]

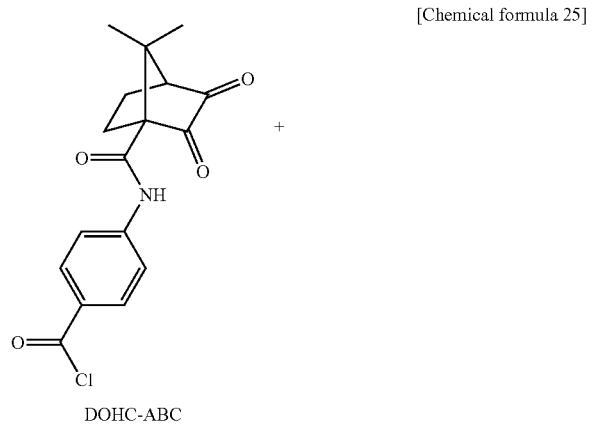

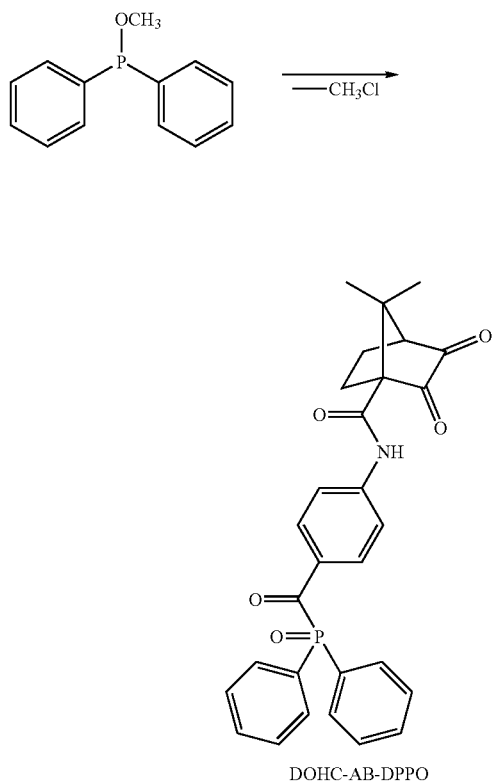

The title compound was synthesized by reacting 3.0 g (9.0 mmol) of acid chloride (DOHC-ABC) synthesized in Step 2 with 2.0 g (9.3 mmol) of methoxydiphenyl phosphite in toluene (30 mL) at 65° C. for 10 hours in a dark chamber. A reaction time was determined by a time at which 1748.55 cm$^{-1}$ (vC=O of COCl) on an IR spectrum completely disappeared. After completion of the reaction, vC=O (1700.32 cm$^{-1}$) and vP=O (1176.13 cm$^{-1}$) of acylphosphine oxide were generated. The reaction mixture was concentrated, placed into a large amount of hexane (200 mL), and a precipitate was filtered, and washed to obtain 3.14 g (yield 69%) of the title compound (DOHC-AB-DPPO) as a pale yellow crystal.

The product showed a pale yellow crystal which was less yellowish than CQ of a yellow crystal.

Melting point: 96-98° C.

IR spectrum (neat: cm$^1$): 1700.32[vC=O of —(C=O)—P(=O)<], 1176.13[vP=O of —(C=O)—P(=O)<]

Elementary analysis: for $C_{29}H_{26}NO_5P$, cal'd: C, 69.73%; H, 5.25%; N, 2.80% found: C, 69.38%; H, 5.51%; N, 2.84%

Ultraviolet-visible spectrum (solvent: toluene): Wide absorption was exhibited at 350-500 nm, and 350 to 420 nm derived from an acylphosphine oxide group and 400 to 500 nm derived from a camphorquinone group were recognized.

From the above analysis results, a structure of the title compound DOHC-AB-DPPO was determined as follows:

[Chemical formula 26]

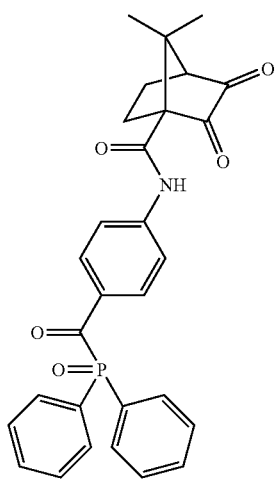

Examples 3 to 4, Comparative Examples 1 to 3

A photopolymerization initiator selectively containing the camphorquinone derivative having an acylphosphine oxide group of the present invention synthesized in Examples 1 to 2 (DOHC-DPPO, DOHC-AB-DPPO), D,L-camphorquinone (CQ), and acylphosphine oxide (TMP-APO), and a radical polymerizable monomer (Bis-GMA, TEGDMA) were prepared into a uniform solution having a composition shown in Table 1, to obtain a photohardenable composition, which was assessed for photohardenabitily with a halogen and LED dental light irradiator, and a color tone, and a change in a color tone were measured. Results are shown in Table 1.

From Table 1, in the conventional CQ alone (Comparative Example 1), photohardenability with Hal and LED is insufficient and a b value indicating a tinge of yellow of a color tone exhibited excessively high 84.0. In TMP-APO alone (Comparative Example 2), no photohardenability with LED was exhibited. In addition, in a mixed system of CQ and TMP-APO (Comparative Example 3), improvement was recognized in photohardenability, but a b value indicating a tinge of yellow of a color tone exhibited excessively high 87.8.

On the other hand, in DOHC-DPPO alone or DOHC-AB-DPPO alone (Examples 3, 4), photohardenability with Hal and LED was found to be more excellent than CQ alone and TMP-APO alone. Further, surprisingly, in DOHC-DPPO, a b value indicating a tinge of yellow of a color tone showed excessively low 4.0, and showed excellent color tone property being about ½₀ of a b value of CQ alone or about ½₂ of a b value of a CQ and TMP-APO mixed system. In Comparative Example 3 in which CQ and TMP-APO are physically mixed, a great b value was not improved at all, while in the compound of the present invention, DOHC-DPPO, an camphorquinone group and an acylphosphine oxide group are chemically bound in a molecule, and excellent photohardenability and excellent color tone stability were generated by structural property having an α-diketone group and an acylphosphine oxide group in a molecule. In addition, a b value of DOHC-AB-DPPO showed a greater value than that of DOHC-DPPO, showed 1/4.6 of CQ alone or a TMP-APO mixed system, and showed a smallest value in ΔE value and Δb value. A remarkable difference in a L value, and a value was not recognized in four samples.

Examples 5 to 6, Comparative Examples 4 to 5

A photohardenable composition consisting of a photopolymerization initiator comprising (A) a camphorquinone derivative having an acylphosphine oxide group (DOHC-DPPO, DOHC-AB-DPPO) as an indispensable component and, further, consisting of (B) aromatic tertiary amine (DMBE) and a radical polymerizable monomer (Bis-GMA, TEGDMA) was prepared into a uniform solution at a composition shown in Table 2, photohardenability was assessed, and light DSC indicating a photopolymerization speed, a usable time which is assessment of operability under ambient light, a color tone, and a change in a color tone were measured. As a control, the previous photopolymerization initiator consisting of CQ, TMP-APO, and DMBE was used. Results are shown in Table 2.

TABLE 1

| | | Example | | Comparative Example | | |
|---|---|---|---|---|---|---|
| Component and photohardenability | | 3 | 4 | 1 | 2 | 3 |
| Photopolymerization initiator | DOHC-DPPO [g] | 2.0 | — | — | — | — |
| | DOHC-AB-DPPO [g] | — | 2.0 | — | — | — |
| | CQ [g] | — | — | 2.0 | — | 2.0 |
| | TMP-APO [g] | — | — | — | 1.0 | 1.0 |
| Radical polymerizable monomer | Bis-GMA [g] | 60 | 60 | 60 | 60 | 60 |
| | TEGDMA [g] | 40 | 40 | 40 | 40 | 40 |
| Photo hardenability | Halogen [30 sec] | ◉ | ◉ | Δ | ◉ | ◉ |
| | LED [10 sec] | ○ | ○ | Δ | X | Δ |
| Time and change in color tone | L value (immediately after photohardening) | 86.1 | 85.1 | 83.7 | 86.2 | 83.4 |
| | a value (immediately after photohardening) | −3.6 | −7.8 | −17.0 | −4.6 | −17.7 |
| | b value (immediately after photohardening) | 4.0 | 18.2 | 84.0 | 6.1 | 87.8 |
| | ΔE (after 1 day at 70° C.) | 1.4 | 0.5 | 1.5 | 0.4 | 2.3 |
| | Δb (after 1 day at 70° C.) | 1.4 | −0.2 | 1.4 | 0.3 | 0.8 |

TABLE 2

| Component and photohardenability | | Example 5 | Example 6 | Comparative Example 4 | Comparative Example 5 |
|---|---|---|---|---|---|
| Photopolymerization initiator | DOHC-DPPO [g] | 2.0 | — | — | — |
| | DOHC-AB-DPPO [g] | — | 2.0 | — | — |
| | CQ [g] | — | — | 2.0 | 2.0 |
| | TMP-APO [g] | — | — | — | 1.0 |
| | DMBE [g] | 1.0 | 1.0 | 1.0 | 1.0 |
| Radical polymerizable monomer | Bis-GMA [g] | 60 | 60 | 60 | 60 |
| | TEGDMA [g] | 40 | 40 | 40 | 40 |
| Photohardenability | Halogen [30 sec] | ◎ | ◎ | ◎ | ◎ |
| | LED [10 sec] | ◎ | ◎ | ◎ | ◎ |
| | Xe [3 sec] | ◎ | ◎ | ◎ | ◎ |
| | light DSC [sec] | 9.6 | 15.4 | 10.9 | 8.5 |
| | Usable time [sec] | 50 | 150 | 5 | 5 |
| Color tone and change in color tone | L (immediately after photohardening) | 86.2 | 84.6 | 83.1 | 82.9 |
| | a (immediately after photohardening) | −4.2 | −7.9 | −16.7 | −16.6 |
| | b (immediately after photohardening) | 6.4 | 20.0 | 83.1 | 88.8 |
| | ΔE (after 1 day at 70° C.) | 2.7 | 0.4 | 4.6 | 6.8 |
| | Δb (after 1 day at 70° C.) | 2.6 | −0.2 | 0.9 | 0.6 |

From Table 2, CQ/DMBE (Comparative Example 4) and CQ/DMBE/TMP-APO (Comparative Example 5) which are the conventional initiators showed a rapid photohardening rate of 8.5 to 10.9 seconds in light DSC, on the other hand, showed a very short usable time of 5 seconds, further, a great difference was not recognized in a L value, but extremely great 83.1 to 88.8 was shown in a b value indicating a tinge of yellow of a color tone, and it was confirmed that there is a decisive defect in operability and a color tone under ambient light as a dental resin.

On the other hand, a photoinitiator consisting of DOHC-DPPO and DMBE of the present invention (Example 5) showed a rapid photopolymerization rate (9.6 seconds), and showed a relaxed usable time (50 seconds). Further, a b value indicating a tinge of yellow of a color tone exhibited extremely small 6.4, being about 1/13 of Comparative Examples 4 to 5, thus, a color tone was considerably improved. Also in the compound of the present invention, DOHC-AB-DPPO, the same tendency as that of DOHC-DPPO was exhibited and, further, a ΔE value and a Δb value showed a minimum value.

Examples 7 to 16 and Comparative Examples 6 to 8

A photohardenable composition consisting of a photopolymerization initiator comprising (A) a camphorquinone derivative having an acrylphosphine oxide group (DOHC-DPPO, DOHC-AB-DPPO) as an indispensable component and, further, comprising by selecting one or more of (B) aromatic tertiary amine (DMBE), a barbiaturic acid derivative (TMBA), a trihalomethyl group-substituted-1,3,5-triazine compound (TCT, MCT), and (bis)acylphosphine oxides (TMP-APO, Bis-TMP-APO), and containing Bis-GMA- and TEGDMA as a radical polymerizable monomer (resin) were prepared into a uniform solution at a composition shown in Table 2, photohardenability was assessed with three kinds of dental light irradiators, light DSC was measured, and a usable time was measured. As a control, the conventional TMP-APO only, and a mixed photopolymerization initiator of CQ/TMP-TMBA and CQ/TMBA/TMP-APO were used. Measurement results are shown in Table 3.

TABLE 3

| Component and photohardenability | | | Example 7 | Example 8 | Example 9 | Example 10 | Example 11 | Example 12 | Example 13 | Example 14 | Example 15 | Example 16 | Comparative Example 6 | Comparative Example 7 | Comparative Example 8 |
|---|---|---|---|---|---|---|---|---|---|---|---|---|---|---|---|
| Photopolymerization initiator | A | DOHC-DPPO [g] | 2.0 | 2.0 | 2.0 | 2.0 | 2.0 | 2.0 | 2.0 | — | — | 1.0 | — | — | — |
| | | DOHC-AB-DPPO [g] | — | — | — | — | — | — | — | 2.0 | 2.0 | 1.0 | — | — | — |
| | B | CQ [g] | — | — | — | — | — | — | — | — | — | — | — | 2.0 | 2.0 |
| | | TCT [g] | — | — | 1.0 | 1.0 | — | 1.0 | — | 1.0 | — | 1.0 | — | — | — |
| | | MCT [g] | — | — | — | — | 1.0 | — | 1.0 | — | 1.0 | — | — | — | — |
| | | TMBA [g] | 1.0 | — | — | — | — | — | — | — | — | — | — | 1.0 | 1.0 |
| | | DMBE [g] | — | 1.0 | — | — | — | — | — | — | — | — | — | — | — |
| | | TMP-APO [g] | — | 1.0 | — | 1.0 | 1.0 | — | — | — | — | — | 1.0 | — | 1.0 |
| | | Bis-TMP-APO [g] | — | — | — | — | — | 1.0 | 1.0 | 1.0 | 1.0 | 1.0 | — | — | — |
| Resin | | Bis-GMA [g] | 60 | 60 | 60 | 60 | 60 | 60 | 60 | 60 | 60 | 60 | 60 | 60 | 60 |
| | | TEGDMA [g] | 40 | 40 | 40 | 40 | 40 | 40 | 40 | 40 | 40 | 40 | 40 | 40 | 40 |
| Photohardenability | | Hal [30 sec] | ◎ | ◎ | ◎ | ◎ | ◎ | ◎ | ◎ | ◎ | ◎ | ◎ | ◎ | ◎ | ◎ |
| | | LED [10 sec] | ◎ | ◎ | ◎ | ◎ | ◎ | ◎ | ◎ | ◎ | ◎ | ◎ | X | ◎ | ◎ |

TABLE 3-continued

| Component and photohardenability | Example | | | | | | | | | | Comparative Example | | |
|---|---|---|---|---|---|---|---|---|---|---|---|---|---|
| | 7 | 8 | 9 | 10 | 11 | 12 | 13 | 14 | 15 | 16 | 6 | 7 | 8 |
| Xe [3 sec] | ◉ | ◉ | ◉ | ◉ | ◉ | ◉ | ◉ | ◉ | ◉ | ◉ | X | ◉ | ◉ |
| Light DSC[sec] | 9.0 | 8.7 | 10.6 | 8.3 | 8.5 | 7.3 | 7.4 | 7.4 | 7.5 | 7.3 | 8.4 | 10.8 | 9.0 |
| Usable time [sec] | 50 | 45 | 150 | 70 | 70 | 35 | 35 | 40 | 40 | 40 | 80 | 10 | 10 |

From Table 3, all of various photopolymerization initiators (Examples 7 to 16) comprising DOHC-DPPO and DOHC-AB-DPPO of the present invention as an indispensable component, and jointly using one or more of an aromatic tertiary amine compound (DMBE), a barbituric acid derivative (TMBA), a trihalomethyl group-substituted-1,3,5-triazine compound (TCT, MCT) and (bis)acylphosphine oxides (TMP-APO, Bis-TMP-APO) showed excellent photopolymerizability with three kinds of dental irradiators (halogen, xenon, LED irradiator) and, further, showed an extremely rapid hardening rate (light DSC: 7.3 to 10.6 seconds), and a relaxed usable time (35 to 150 seconds).

On the other hand, the conventional TMP-APO alone (Comparative Example 6) showed excellent photopolymerizability and a rapid photohardening rate with Hal, but showed no photohardenability with LED and Xe. A mixed system of CQ/TMBA and CQ/TMBA/TMP-APO (Comparative Examples 7, 8) showed excellent photopolymerizability and a rapid hardening rate (light DSC: 9.0 to 10.8 seconds) with three kinds of dental irradiators, but showed a very short usable time (10 seconds), and it was suggested that operability under ambient light is difficult.

Examples 17 to 27

A photohardenable composition consisting of a photopolymerization initiator containing (A) a camphorquinone derivative (DOHC-DPPO) having an acylphosphine oxide group as an indispensable component, and containing selectively one or more of (B) an organotin compound (Tin-Lau) and (bis)acylphosphine oxides (TMP-APO, Bis-TMP-APO), and Bis-GMA, TEGDMA, and 4-AET as a radical polymerizable monomer (resin) was prepared into a uniform solution at a composition shown in Table 3, photohardenability was assessed with three kinds of dental light irradiators, light DSC was measured, a usable time, and a color tone and a color difference after 1 day at 70° C. were measured. Results are shown in Table 4.

TABLE 4

| Component and photohardenability | | | Example | | | | | | | | | | | |
|---|---|---|---|---|---|---|---|---|---|---|---|---|---|---|
| | | | 17 | 18 | 19 | 20 | 21 | 22 | 23 | 24 | 25 | 26 | 27 |
| Photopolymerization initiator | A | DOHC-DPPO [g] | 2.5 | 2.5 | 2.5 | 2.5 | 2.5 | 2.5 | 2.5 | 2.5 | 2.5 | 2.5 | 2.5 |
| | B | Tin-Lau [g] | 1.5 | 1.5 | 1.5 | 1.5 | 1.5 | 1.5 | 1.5 | 1.5 | 1.5 | 1.5 | 1.5 |
| | | TMP-APO [g] | — | 0.05 | 0.1 | 0.3 | 0.5 | 1.0 | — | — | — | — | — |
| | | Bis-TMP-APO [g] | — | — | — | — | — | — | 0.05 | 0.1 | 0.3 | 0.5 | 1.0 |
| Resin | | Bis-GMA [g] | 60 | 60 | 60 | 60 | 60 | 60 | 60 | 60 | 60 | 60 | 60 |
| | | TEGDMA [g] | 40 | 40 | 40 | 40 | 40 | 40 | 40 | 40 | 40 | 40 | 40 |
| | | 4-AET [g] | 0.5 | 0.5 | 0.5 | 0.5 | 0.5 | 0.5 | 0.5 | 0.5 | 0.5 | 0.5 | 0.5 |
| Photohardenability | | Hal [30 sec] | ◉ | ◉ | ◉ | ◉ | ◉ | ◉ | ◉ | ◉ | ◉ | ◉ | ◉ |
| | | LED [10 sec] | ◉ | ◉ | ◉ | ◉ | ◉ | ◉ | ◉ | ◉ | ◉ | ◉ | ◉ |
| | | Xe [3 sec] | ◉ | ◉ | ◉ | ◉ | ◉ | ◉ | ◉ | ◉ | ◉ | ◉ | ◉ |
| | | Light DSC [sec] | 10.9 | 9.7 | 9.3 | 8.7 | 8.9 | 9.0 | 8.7 | 7.9 | 7.3 | 7.3 | 7.3 |
| | | Usable time [sec] | 150 | 130 | 110 | 80 | 70 | 50 | 100 | 70 | 50 | 35 | 35 |
| Color tone | | L (immediately after photohardening) | 86.0 | 86.2 | 85.5 | 85.5 | 85.6 | 85.4 | 85.5 | 85.6 | 85.0 | 84.9 | 84.3 |
| | | a (immediately after photohardening | −5.7 | −4.9 | −5.1 | −5.7 | −6.2 | −6.6 | −5.1 | −6.1 | −8.2 | −10.0 | −11.9 |
| | | b (immediately after photohardening | 10.2 | 8.7 | 9.0 | 10.4 | 11.4 | 12.6 | 8.9 | 11.3 | 16.3 | 20.5 | 26.2 |
| | | ΔE after 1 day at 70° C. | 4.5 | 4.9 | 5.2 | 4.5 | 4.6 | 4.8 | 5.3 | 4.0 | 5.1 | 5.1 | 5.0 |
| | | Δb after 1 day at 70° C. | 4.3 | 4.7 | 5.0 | 4.4 | 4.5 | 4.7 | 5.1 | 3.9 | 5.0 | 5.1 | 3.3 |

From Table 4, DOHC-DPPO/Tin-Lau, DOHC-DPPO/Tin-Lau/TMP-APO and DOHC-DPPO/Tin-Lau/Bis-TMP-APO which are photopolymerization initiators of the present invention showed excellent photohardenability with three kinds of dental irradiators, and showed a rapid photopolymerization rate (light DSC: 7.3 to 10.9 seconds) and a relaxed usable time (35 to 150 seconds). There was a tendency that as an addition amount of TMP-APO or Bis-TMP-APO is increased, a usable time is shorter, and there was a tendency that as an addition amount of Bis-TMP-APO is increased, a b value is increased. However, a color difference after 1 day at 70° C. of a hardened product showed 4.0 to 10.9 as expressed by ΔE, and 3.2 to 5.0 as expressed by a Δb value, both being a small value. From these results, a photoinitiator containing DOHC-DPPO as an indispensable component and combined with one or more of Tin-Lau, TMP-APO and Bis-TMP-APO, sufficiently satisfied a photopolymerization rate, a usable time and color tone stability which are an object of the present invention

Examples 28 to 32

A photohardenable composition comprising the photopolymerization initiator of the present invention was studied as an aspect of a photopolymerizable composite resin for a crown and a bridge of a tooth crown. A photopolymerization initiator containing (A) DOHC-DPPO as an indispensable component, and selectively containing one or more of (B) Tin-Lau, TMP-APO, and Bis-TMP-APO, and UDMA, TMPT and 4-AET as a radical polymerizable monomer were mixed at a composition of Table 3 to prepare matrix resin compositions. To all composition solutions was added butylated hydroxytoluene (380 ppm).

Then, the matrix resin composition, a silica filler (average particle size: 3 μm) and a ultrafine particle filler (manufactured by NIPPON AEROSIL CO., LTD.) were mixed at a composition of Table 5, uniformly kneaded with a kneader, and defoamed to produce photopolymerization composite resins for a crown and a bridge of a tooth crown. In preparation of a paste, a minor amount of a pigment as incisal shade was added. Photopolymerizability of the photopolymerization composite resin was assessed with three kinds of dental light irradiators, light DSC was measured, and a usable time, a flexural strength, an elastic modulus, and a color tone and a color difference after 1 day at 70° C. of a hardened product were measured. Results are shown in Table.

TABLE 5

| Component and photohardenability | | Example 28 | 29 | 30 | 31 | 32 |
|---|---|---|---|---|---|---|
| Photoinitiator | A DOHC-DPPO [g] | 2.5 | 2.5 | 2.5 | 2.5 | 2.5 |
| | B Tin-Lau [g] | 1.5 | 1.5 | 1.5 | 1.5 | 1.5 |
| | TMP-APO [g] | — | 0.5 | 1.0 | — | — |
| | Bis-TMP-APO [g] | — | — | — | 0.1 | 0.3 |
| Radical polymerizable monomer | UDMA [g] | 60 | 60 | 60 | 60 | 60 |
| | TMPT [g] | 40 | 40 | 40 | 40 | 40 |
| | 4-AET [g] | 0.5 | 0.5 | 0.5 | 0.5 | 0.5 |
| Filler | Silica filler [g] | 271.4 | 271.4 | 271.4 | 271.4 | 271.4 |
| | Fine particle filler [g] | 8.4 | 8.4 | 8.4 | 8.4 | 8.4 |
| Photohardenability | Hal [30 sec] | ◎ | ◎ | ◎ | ◎ | ◎ |
| | LED [10 sec] | ◎ | ◎ | ◎ | ◎ | ◎ |
| | Xe [3 sec] | ◎ | ◎ | ◎ | ◎ | ◎ |
| | Light DSC [sec] | 14.4 | 9.6 | 10.5 | 12.4 | 9.8 |
| | Usable time [sec] | 150 | 150 | 140 | 150 | 130 |
| Mechanical strength | Flexural strength (MPa) | 114.3 | 122.1 | 113.5 | 123.6 | 123.4 |
| | Elastic modulus (GPa) | 10.2 | 11.6 | 12.3 | 11.7 | 12.3 |
| Tone | b value (immediately after photohardening) | 16.7 | 18.3 | 18.7 | 17.7 | 19.9 |
| | ΔE value (color difference after 1 day at 70° C.) | 1.2 | 0.6 | 0.7 | 0.8 | 0.7 |
| | Δb value (color difference after 1 day at 70° C.) | 0.4 | −0.3 | −0.3 | 0.0 | −0.5 |

From Table 5, in the photohardenable composition containing the photopolymerization initiator of the present invention, photohardenability with three kinds of irradiators is excellent, a photohardening time is short, a relaxed usable time of 150 seconds is exhibited, further as a color tone, a low b value is exhibited and, at the same time, results that a ΔE value and a Δb value are very small, indicating a change in a color tone, are exhibited, and the excellent effect as a photopolymerization composite resin for a crown and a bridge of a tooth crown attaching importance to aesthetic property was recognized.

From the above results, it was confirmed that the photopolymerization initiator of the present invention imparts stable performance such as a rapid photohardening rate and excellent photopolymerizability, relaxed operability, and physical property to a composite resin for a crown and a bridge of a tooth crown.

Examples 33 to 43

A photopolymerizable composition consisting of a photopolymerization initiator comprising (A) DOHC-DPPO as an indispensable component, and comprising one or more selected from (B) Tin-Lau, TMP-APO, Bis-TMP-APO, and CQ, and Bis-GMA, TEGDMA, and 4-AET as a radical polymerizable monomer (resin) was prepared into a uniform solution at a composition shown in Table 6, photohardenability with three kinds of dental light irradiators was assessed, light DSC was measured, and a usable time, and a color difference after 1 day at 70° C. of a hardened product were measured. Results are shown in Table 6.

TABLE 6

| Component and photohardenability | | Example | | | | | | | | | | |
|---|---|---|---|---|---|---|---|---|---|---|---|---|
| | | 33 | 34 | 35 | 36 | 37 | 38 | 39 | 40 | 41 | 42 | 43 |
| Photoinitiator | A DOHC-DPPO [g] | 0.05 | 0.1 | 0.5 | 1.0 | 1.5 | 0.05 | 0.1 | 0.5 | 1.0 | 1.5 | 0.5 |
| | B Tin-Lau [g] | 1.5 | 1.5 | 1.5 | 1.5 | 1.5 | 1.5 | 1.5 | 1.5 | 1.5 | 1.5 | 1.5 |
| | TMP-APO [g] | 0.5 | 0.4 | 0.3 | 0.2 | 0.1 | — | — | — | — | — | — |
| | Bis-TMP-APO [g] | — | — | — | — | — | 0.5 | 0.4 | 0.3 | 0.2 | 0.1 | 0.05 |
| | CQ [g] | 0.1 | 0.1 | 0.1 | 0.1 | 0.1 | 0.1 | 0.1 | 0.1 | 0.1 | 0.1 | 0.1 |
| Resin | Bis-GMA [g] | 60 | 60 | 60 | 60 | 60 | 60 | 60 | 60 | 60 | 60 | 60 |
| | TEGDMA [g] | 40 | 40 | 40 | 40 | 40 | 40 | 40 | 40 | 40 | 40 | 40 |
| | 4-AET [g] | 0.5 | 0.5 | 0.5 | 0.5 | 0.5 | 0.5 | 0.5 | 0.5 | 0.5 | 0.5 | 0.5 |
| Photohardenability | Hal [30 sec] | ⊚ | ⊚ | ⊚ | ⊚ | ⊚ | ⊚ | ⊚ | ⊚ | ⊚ | ⊚ | ⊚ |
| | LED [10 sec] | ⊚ | ⊚ | ⊚ | ⊚ | ⊚ | ⊚ | ⊚ | ⊚ | ⊚ | ⊚ | ⊚ |
| | Xe [3 sec] | ⊚ | ⊚ | ⊚ | ⊚ | ⊚ | ⊚ | ⊚ | ⊚ | ⊚ | ⊚ | ⊚ |
| | Light DSC [sec] | 9.2 | 9.4 | 9.6 | 9.9 | 10.5 | 7.9 | 8.1 | 8.5 | 8.9 | 9.6 | 10.4 |
| | Usable time [sec] | 95 | 100 | 11.0 | 125 | 140 | 40 | 50 | 60 | 75 | 100 | 120 |
| Color tone | L (immediately after photo hardening) | 86.0 | 86.2 | 86.1 | 86.1 | 86.0 | 85.9 | 86.1 | 86.1 | 86.1 | 86.1 | 86.1 |
| | a (immediately after photo hardening) | −9.4 | −9.3 | −9.6 | −9.9 | −10 | −13 | −12 | −13 | −13 | −11 | −9.3 |
| | b (immediately after photo hardening) | 9.8 | 9.6 | 10.6 | 11.9 | 12.5 | 19.0 | 17.9 | 18.6 | 17.9 | 15.2 | 5.2 |
| | ΔE after 1 day at 70° C. | 2.7 | 2.8 | 3.6 | 4.4 | 5.3 | 4.7 | 5.4 | 5.0 | 5.4 | 5.8 | 3.1 |
| | Δb after 1 day at 70° C. | 1.8 | 2.6 | 2.4 | 4.2 | 5.0 | 3.8 | 4.9 | 4.3 | 4.9 | 5.3 | 2.9 |

The photopolymerization initiator of the present invention consisting of a combination of Table 6 containing DOHC-DPPO as an indispensable component exhibits excellent polymerizability with all of three kinds of dental irradiators, exhibits light DSC: 7.9 to 10.5 seconds, a usable time: 40 to 140 seconds, a b value: 5.2-20.3, ΔE after 1 day at 70° C.: 2.7 to 5.8, and Δb: 1.8-5.3 and, by increasing and decreasing a concentration of DOHC-DPPO and an initiator component in Table, a hardenable composition having better balance between a photohardening rate, a usable time, a color tone, and a change in a color tone can be designed.

Examples 44 to 45, and Comparative Examples 9 to 11

A mixture containing a matrix resin (26 parts by weight) consisting of UDMA (60 parts by weight), TMPT (40 parts by weight), and 4-AET (0.4 part by weight), a silica filler (72.9 parts by weight), a fine particle filler (1.1 parts by weight), and a photopolymerization initiator was kneaded with a kneader to produce a photopolymerization composite resin. In production of a paste, a minor amount of a pigment as incisal shade was added. As the photopolymerization initiator, DOHC-DPPO, DOHC-AB-DPPO, CQ, TMP-APO, and DMBE were prepared at a composition shown in Table 7 based on 100 parts by weight of the matrix resin. A hardening depth, a usable time, a flexural strength, an elastic modulus of the prepared photopolymerization composite resin were measured, and a change in a color tone was assessed. Results are shown in Table 7

TABLE 7

| Photopolymerization initiator, and photo hardening property and change in color tone | | | Example | | Comparative Example | | |
|---|---|---|---|---|---|---|---|
| | | | 44 | 45 | 9 | 10 | 11 |
| Photopolymerization initiator | A | DOHC-DPPO (parts by weight) | 2.0 | — | — | — | — |
| | | DOHC-AB-DPPO (parts by weight) | — | 2.0 | — | — | — |
| | B | CQ (parts by weight) | — | — | 2.0 | — | 2.0 |

TABLE 7-continued

| | Photopolymerization initiator, and photo hardening property and change in color tone | Example 44 | Example 45 | Comparative Example 9 | Comparative Example 10 | Comparative Example 11 |
|---|---|---|---|---|---|---|
| | TMP-APO (parts by weight) | — | — | — | 2.0 | 2.0 |
| | DMBE (parts by weight) | 0.6 | 0.6 | 0.6 | — | 0.6 |
| Photohardening property and Color tone | Hardening depth (halogen 30 sec) (mm) | 8.0 | 8.0 | 7.0 | 4.6 | 8.0 |
| | Hardening depth (LED 10 sec) (mm) | 8.0 | 8.0 | 6.0 | 0 | 8.0 |
| | Hardening depth (LED 15 sec) (mm) | 8.0 | 8.0 | 6.3 | 0 | 8.0 |
| | Hardening depth (LED 20 sec) (mm) | 8.0 | 8.0 | 7.5 | 0 | 8.0 |
| | Flexural strength (MPa) | 95 | 96 | 90 | 85 | 98 |
| | Elastic modulus (GPa) | 7.5 | 7.6 | 6.8 | 6.7 | 7.9 |
| | Usable time (sec) | 35 | 35 | 10 | 150 | 3 |
| | Change in color tone ΔE value (color difference before and after photohardening) | 3.5 | 3.7 | 8.0 | 3.8 | 14.5 |
| | Color tone  Before photohardening | 13.5 | 13.9 | 18.5 | 11.0 | 27.0 |
| | b value    After photohardening | 12.0 | 12.0 | 11.0 | 10.0 | 13.5 |
| | Change in color tone Δb value (color difference before and after photohardening) | 1.5 | 1.9 | 7.5 | 1.0 | 13.5 |

From results of Table 7, when the conventional CQ/DMBE was used (Comparative Example 9), a hardening depth and a flexural strength were relatively low, and a high ΔE value of 8.0 and a high Δb value of 7.5 were exhibited, and a usable time of 10 seconds was exhibited, suggesting that an operation time is short. In the case of only TMP-APO (Comparative Example 10), a hardening depth was 4.6 mm with a halogen lamp, but 0 mm with LED. Physical property with a halogen lamp was at a CQ level. When a ternary mixed system of CQ/TMP-APO/DMBE was used (Comparative Example 11), a high value was exhibited in a hardening depth and a flexural strength but a usable time was considerably short, exhibiting 3 seconds, and this was determined to be not practical. In addition, as for a color difference before and after photohardening, a ΔE value exhibited 14.5, and a Δb value exhibited 13.5, and it was suggested that there is a decisive defect in a color tone of a dental composite resin.

On the other hand, in the case of the photoinitiator of the present invention (Examples 44-45), a hardening depth and a flexural strength were excellent, a ΔE value of 3.5 to 3.7, and a Δb value of 1.5 to 1.9 were exhibited, and a usable time of 35 to 40 seconds was exhibited, thus, stable performance was exhibited. Originally, since CQ has a strong stinge of yellow, photohardenability is adjusted suitable by reducing an addition amount thereof, but it was made clear that DOHC-DPPO, and DOHC-AB-DPPO of the present invention are excellent in color tone stability also at a high concentration as compared with the previous CQ.

That is, DOHC-DPPO and DOHC-AB-DPPO of the present invention have an α-diketone group derived from camphorquinone and an acylphosphine group in each molecule, are novel compounds having wide absorption in a near ultraviolet-visible region from their structural property, a photopolymerization initiator containing these compounds as an indispensable component exhibits excellent photopolymerizability with three kinds of dental irradiators (halogen, xenon, LED), and it was made clear that they have an extremely excellent color tone of a hardened product as compared with the conventional CQ. Further, they have rapid photohardening property, and operability stable under ambient light, have a stable physical nature such as a hardening depth and a flexural strength, and use in the dental field can be greatly expected.

Example 46

A resin cement liquid agent consisting of Bis-GMA (30 parts by weight), EDMA (35 parts by weight), TEGDMA (20 parts by weight), EGDMA (7.0 parts by weight), 6-MHPA (5 parts by weight), DOHC-DPPO (2.0 parts by weight), CQ (0.5 part by weight), BPO (0.5 part by weight), and BHT (500 ppm), and a resin cement powder agent consisting of a silica filler (98.9 parts by weight), BPBA (1 part by weight), and DEPT (0.1 part by weight) were prepared. The prepared photo/chemical polymerization resin cement was hardened in 6.5 minutes when mixed at a powder/liquid ratio of 3.5/1.0 in a dark chamber at 23±1° C. In addition, when a cement mud immediately after mixing was irradiated with Shofu Grip Light II [manufactured by SHOFU INC.] which is a halogen lamp (Hal) irradiator, it was hardened in 10 seconds. An experimentally manufactured cement was mixed and, after chemical polymerization, subjected to photo/chemical polymerization (dual curing). A flexural strength was exhibited to be 118 MPa, and an elastic modulus was exhibited to be 86 GPa after 24 hours at 37° C. in water.

INDUSTRIAL APPLICABILITY

The present invention can be, applied not only to the dental field and orthopedic field, but also to the photopolymerization industry field such as an adhesive, a paint, printing, a printed-circuit board, and a photoresist.

The invention claimed is:

1. A camphorquinone derivative having an acylphosphine oxide group [—(C=O)—(P=O)< in each molecule.

2. The camphorquinone derivative having an acylphosphine oxide group in each molecule according to claim 1, which is represented by the following general formula (I):

[Chemical formula 1]

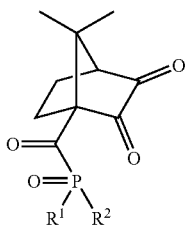

(I)

[wherein, $R^1$ is an alkyl group, an alkoxy group, or an aromatic group, each group optionally having a substituent; $R^2$ is the same as or different from $R^1$, and is an alkyl group, an alkoxy group, or an aromatic group, each group optionally having a substituent, or an —OM group, wherein, M is an alkali metal or an alkaline earth metal] and which may be a D body or a L body.

3. The camphorquinone derivative having an acylphosphine oxide group in each molecule according to claim 1, which is represented by the following general formula (II):

[Chemical formula 2]

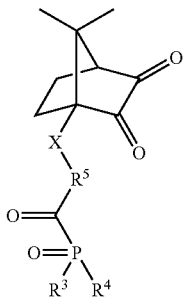

(II)

[wherein $R^3$ is an alkyl group, an alkoxy group or an aromatic group, each group optionally having a substituent; $R^4$ is the same as or different from $R^3$, and is an alkyl group, an alkoxy group or an aromatic group, each group optionally having a substituent, or an —OM group, wherein M is an alkali metal or an alkaline earth metal; $R^5$ is a carbon atom having an aromatic group optionally having a substituent and a C2 to 18 linear chain, or a substituent, as a functional group; and X is an amide bond or an ester bond] and which may be a D body or a L body.

4. A photopolymerization initiator, comprising the camphorquinone derivative having an acylphosphine oxide group [—(C=O)—(P=O)< in each molecule as defined in claim 1 as an indispensable component.

5. A photopolymerization initiator which comprises (A) the camphorquinone derivative having an acylphosphine oxide group [—(C=O)—(P=O)< in each molecule as defined in claim 1 as an indispensable component and, further, comprises (B) one or more selected from a polymerization accelerator, a photoacid generator, a photosensitizer, and (bis)acylphosphine oxide.

6. The photopolymerization initiator according to claim 5, wherein the polymerization accelerator is selected from the group consisting of an amine compound, a barbituric acid derivative and an organotin compound, the photoacid generator is selected form the group consisting of trihalomethyl group-substituted-1,3,5-triazine compounds, the photosensitizer is an α-diketone compound, and the (bis)acylphosphine oxide is selected from the group consisting of an acylphosphine oxide compound and a bisacylphosphine oxide compound.

7. A photo/chemical polymerization initiator, comprising the photopolymerization initiator as defined in claim 4 and, further, comprising a room temperature polymerization initiator, thereby, enabling to initiate chemical polymerization and photopolymerization.

8. A hardenable composition, containing the photopolymerization initiator as defined in claim 4, and a radical polymerizable monomer.

9. A hardenable composition, containing the photo/chemical polymerization initiator as defined in claim 7 and a radical polymerizable monomer.

10. The hardenable composition according to claim 8, further containing a filler.

11. The hardenable composition according to claim 8, which is a dental hardenable composition.

12. A photopolymerization initiator, comprising the camphorquinone derivative having an acylphosphine oxide group [—(C=O)—(P=O)< in each molecule as defined in claim 2 as an indispensable component.

13. A photopolymerization initiator, comprising the camphorquinone derivative having an acylphosphine oxide group [—(C=O)—(P=O)< in each molecule as defined in claim 3 as an indispensable component.

14. A photopolymerization initiator which comprises (A) the camphorquinone derivative having an acylphosphine oxide group [—(C=O)—(P=O)< in each molecule as defined in claim 2 as an indispensable component and, further, comprises (B) one or more selected from a polymerization accelerator, a photoacid generator, a photosensitizer, and (bis)acylphosphine oxide.

15. A photopolymerization initiator which comprises (A) the camphorquinone derivative having an acylphosphine oxide group [—(C=O)—(P=O)< in each molecule as defined in claim 3 as an indispensable component and, further, comprises (B) one or more selected from a polymerization accelerator, a photoacid generator, a photosensitizer, and (bis)acylphosphine oxide.

16. A photo/chemical polymerization initiator, comprising the photopolymerization initiator as defined in claim 5 and, further, comprising a room temperature polymerization (chemical polymerization) initiator, thereby, enabling to initiate chemical polymerization and photopolymerization.

17. A photo/chemical polymerization initiator, comprising the photopolymerization initiator as defined in claim 6 and, further, comprising a room temperature polymerization (chemical polymerization) initiator, thereby, enabling to initiate chemical polymerization and photopolymerization.

18. A hardenable composition, containing the photopolymerization initiator as defined in claim 5, and a radical polymerizable monomer.

19. A hardenable composition, containing the photopolymerization initiator as defined in claim 6, and a radical polymerizable monomer.

20. The hardenable composition according to claim 9, further containing a filler.

21. The hardenable composition according to claim 9, which is a dental hardenable composition.

22. The hardenable composition according to claim 10, which is a dental hardenable composition.

* * * * *